(12) United States Patent
Mammedov et al.

(10) Patent No.: US 11,673,926 B2
(45) Date of Patent: Jun. 13, 2023

(54) IN VIVO DE-GLYCOSYLATION OF RECOMBINANT PROTEINS BY CO-EXPRESSION WITH PNGASE F

(75) Inventors: Tarlan Mammedov, Newark, DE (US); Vidadi Yusibov, Havertown, PA (US)

(73) Assignee: IBIO, INC., Bryan, TX (US)

( * ) Notice: Subject to any disclaimer, the term of this patent is extended or adjusted under 35 U.S.C. 154(b) by 696 days.

(21) Appl. No.: 14/124,109

(22) PCT Filed: Jun. 7, 2012

(86) PCT No.: PCT/US2012/041340
§ 371 (c)(1),
(2), (4) Date: Feb. 27, 2014

(87) PCT Pub. No.: WO2012/170678
PCT Pub. Date: Dec. 13, 2012

(65) Prior Publication Data
US 2014/0186886 A1 Jul. 3, 2014

Related U.S. Application Data

(60) Provisional application No. 61/564,427, filed on Nov. 29, 2011, provisional application No. 61/494,141, filed on Jun. 7, 2011.

(51) Int. Cl.
| | | |
|---|---|---|
| C12N 9/80 | (2006.01) | |
| C12N 15/82 | (2006.01) | |
| C07K 14/445 | (2006.01) | |
| C07K 14/32 | (2006.01) | |

(52) U.S. Cl.
CPC ............ *C07K 14/445* (2013.01); *C07K 14/32* (2013.01); *C12N 9/80* (2013.01); *C12N 15/8242* (2013.01)

(58) Field of Classification Search
CPC ...... C12N 9/80; C12N 15/82; C12N 15/8242; C07K 14/445; C07K 14/32
See application file for complete search history.

(56) References Cited

U.S. PATENT DOCUMENTS

| | | |
|---|---|---|
| 5,238,821 A | 8/1993 | Barsomian et al. |
| 5,580,859 A | 12/1996 | Felgner et al. |
| 5,589,466 A | 12/1996 | Felgner et al. |

(Continued)

FOREIGN PATENT DOCUMENTS

| | | |
|---|---|---|
| CN | 103392003 | 11/2003 |
| CN | 1641037 | 7/2005 |

(Continued)

OTHER PUBLICATIONS

Su et al (Enzyme and Microbial Technology, 2007, 40: 1496-1502).*

(Continued)

*Primary Examiner* — Anne Marie Grunberg
(74) *Attorney, Agent, or Firm* — Edwin S. Flores; Daniel J. Chalker; Chalker Flores, LLP

(57) ABSTRACT

Materials and methods for in vivo de-glycosylation of recombinant N-glycosylated proteins by co-expression with bacterial PNGase F (Peptide: N-glycosidase F) in plants, using a transient expression system are described. Methods are described which, for example, produce recombinant proteins of interest in plants in a non-glycosylated form. A method of expressing active bacterial PNGase F in plants also is provided.

9 Claims, 9 Drawing Sheets

Specification includes a Sequence Listing.

(56) References Cited

U.S. PATENT DOCUMENTS

| | | | |
|---|---|---|---|
| 5,888,789 A | 3/1999 | Rodriguez | |
| 5,929,304 A * | 7/1999 | Radin | C12N 15/8237 435/183 |
| 6,500,644 B1 | 12/2002 | Borchert et al. | |
| 7,897,842 B2 * | 3/2011 | Bakker | C12N 15/8243 800/298 |
| 2002/0174453 A1 * | 11/2002 | Daniell | C07K 16/00 800/288 |
| 2004/0092470 A1 | 5/2004 | Leonard et al. | |
| 2009/0274679 A1 * | 11/2009 | Mor | C12N 15/8257 424/94.6 |

FOREIGN PATENT DOCUMENTS

| | | |
|---|---|---|
| CN | 17463 02 | 3/2006 |
| CN | 1793324 | 6/2006 |
| WO | WO 1996/02555 | 2/1996 |
| WO | WO 2000/00624 | 1/2000 |
| WO | WO 2000/20612 | 4/2000 |
| WO | WO-2008151440 A1 * | 12/2008 ......... C12N 15/8245 |

OTHER PUBLICATIONS

Invitrogen Catalog (2002, pYD1 Yeast Display Vector Kit, Catalog No. V835-01, Version D).*
Dafny-Yelin et al (Plant Physiology, 2007, 145(4): 1118-1128).*
Demain et al (Biotechnology Advances, 2009, 27(3): 297-306).*
Agarwal et al (Transgenic Res, 2008, 17: 881-896).*
GenBank EF638827 (published 2008).*
GenBank AAA24932.1 (published 1993).*
Diepold et al (The Plant Journal, 2007, 52(1): 94-104).*
Su et al (Enzyme and Microbial Technology, 2007, 40: 1496-1502; cited on IDS).*
Takos et al (The Plant Journal, 2000, 21(1): 43-52).*
Bakker et al (PNAS, 2006, 103(2): 7577-7582).*
"PNGases: A diverse family of enzymes related by function rather than catalytic mechanism", Jana Filitcheva, 2010, Thesis, Institute of Molecular BioSciences Massey University, New Zealand, p. 24-25.*
Tekoah et al in 2004, "Controlled glycosylation of therapeutic antibodies in plants," Archives of Biochemistry and Biophysics 426 2004, 266-278, downloaded from https://www.sciencedirect.com/science/article/pii/S0003986104001237.*
No References Cited AMG Feb. 2, 2023.*
International Search Report and Written Opinion in International Application No. PCT/US2012/041340, dated Oct. 2, 2012, 15 pages.
International Preliminary Report on Patentability in International Application No. PCT/US2012/041340, dated Dec. 10, 2013, 9 pages.
Agarwal et al., "Expression of modified gene encoding functional human α-1-antitrypsin protein in transgenic tomato plants," Transgenic Res., Mar. 2008, 17(5):881-896.
Bakker et al., "Galactose-extended glycans of antibodies produced by transgenic plants," Proc. Natl. Acad. Sci. USA, 2001, 98(5):2899-2904.
Barfield and Pua, "Gene transfer in plants of *Brassica juncea* using *Agrobacterium tumefaciens* mediated transformation," Plant Cell Reports, 1991, 10(6/7):308-314.
Blake, II et al., "Automated kinetic exclusion assays to quantify protein binding interactions in homogeneous solution," Anal. Biochem., 1999, 272:123-134.
Chen et al., "Complete sequence of the binary vector pBI121 and its application in cloning T-DNA insertion from transgenic plants," Mol. Breeding, 2003, 11:287-293.
Clifton et al. "Folate receptor α: a storied past and promising future in immunotherapy," Hum. Vaccin., 2011, 7:183-190.
De la Riva et al., "*Agrobacterium tumefaciens*: a natural tool for plant transformation," Electronic J. Biotechnol., 1998, 1(3), 15 pages.

Fraley et al., "Expression of bacterial genes in plant cells," Proc. Natl. Acad. Sci. USA, 1983, 80:4803-4807.
Frank et al., "Comparative analyses of *Arabidopsis* complex glycanl mutants and genetic interaction with staurosporin and temperature sensitive3a $1[^{W}][^{OA}]$," Plant Physiol., 2008, 148(3):1354-1367.
Frey et al., "Expression of rat β(1,4)-N-acetylglucosaminyltransferase III in *Nicotiana tabacum* remodels the plant-specific N-glycosylation," Plant Biotechnol. J., 2009, 7(1):33-48.
Gelvin, "Agrobacterium-mediated plant transformation: the biology behind the "gene-jockeying" tool," Microbiol. Mol. Biol. Reviews, 2003, 67(1):16-37.
Genbank® Accession No. AAA22637, Aug. 1999, 1 page.
Genbank® Accession No. EU366251, Mar. 2008, 2 pages.
Genbank® Accession No. J05411, Apr. 1993, 2 pages.
Guo et al., "Aberrant N-glycosylation of $β_1$ integrin causes reduced $α_5β_1$ integrin clustering and stimulates cell migration," Cancer Res., 2002, 62:6837-6845.
Hellens et al., "pGreen: a versatile and flexible binary Ti vector for Agrobacterium-mediated plant transformation," Plant Mol. Biol., 2000, 42:819-832.
Hori and Elbein, "Tunicamycin inhibits glycosylation in suspension cultured soybean cells," Plant Physiol., 1981, 67:882-886.
Isaji et al., "Introduction of bisecting GlcNAc into integrin $α_5β_1$ reduces ligand binding and down-regulates cell adhesion and cell migration," J. Biol. Chem., 2004, 279:19747-19754.
Kapila et al., "An Agrobacterium-mediated transient gene expression system for intact leaves," Plant Sci., 1997, 122:101-108.
Lawton et al., "Expression of a soybean β-conclycinin gene under the control of the Cauliflower Mosaic Virus 35S and 19S promoters in transformed petunia tissues," Plant Mol. Biol., 1987, 9:315-324.
Lemp et al., "Molecular cloning and heterologous expression of N-glycosidase F from *Flavobacterium meningosepticum*," J. Biol. Chem., Sep. 1990, 265(26):15606-15610.
Lorence and Verpoorte, "Gene transfer and expression in plants," Methods Mol. Biol., 2004, 267:329-350.
Matsuo and Matsumura, "Deletion of fucose residues in plant N-glycans by repression of the GDP-mannose 4,6-dehydratase gene using virus-induced gene silencing and RNA interference," Plant Biotechnol. J., 2011, 9(2):264-281.
Misaki et al., "Plant cultured cells expressing human β1,4-galactosyltransferase secrete glycoproteins with galactose-extended N-linked glycans," Glycobiology, 2003, 13(3):199-205.
Nita-Lazar et al., "Overexpression of DPAGT1 leads to aberrant N-glycosylation of E-cadherin and cellular discohesion in oral cancer," Cancer Res., 2009, 69:5673-5680.
Outchkourov et al., "Epitope analysis of the malaria surface antigen pfs48/45 identifies a subdomain that elicits transmission-blocking antibodies," J. Biol. Chem., 2007, 282:17148-17156.
Palacpac et al., "Stable expression of human β1,4-galactosyltransferase in plant cells modifies N-linked glycosylation patterns," Proc. Natl. Acad. Sci. USA, 1999, 96(8):4692-4697.
Partridge et al., "Regulation of cytokine receptors by golgi N-glycan processing and endocytosis," Science, 2004, 306:120-124.
Pilon-Smits et al., "Overexpression of ATP Sulfurylase in Indian mustard leads to increased selenate uptake, reduction, and tolerance," Plant Physiolog., 1999, 119(1):123-132.
Plummer et al., "Demonstration of peptide:N-glycosidase F activity in endo-beta-N-acetylglucosaminidase F preparations," J. Biol. Chem., 1984, 259(17):10700-10704.
Roeffen et al., "*Plasmodium falciparum*: production and characterization of rat monoclonal antibodies specific for the sexual-stage Pfs48/45 antigen," Exp. Parasitol., 2001, 97:45-49.
Roy et al., "A novel two-component Tobacco mosaic virus-based vector system for high-level expression of multiple therapeutic proteins including a human monoclonal antibody in plants," Virology, 2010, 405(1):93-99.
Saint-Jore-Dupas et al., "From planta to pharma with glycosylation in the toolbox," Trends Biotechnol., 2007, 25(7):317-323.
Shoji, et al., "Plant-derived hemagglutinin protects ferrets against challenge infection with the A/Indonesia/05/05 strain of avian influenza," Vaccine, 2009, 27:1087-1092.

(56) References Cited

OTHER PUBLICATIONS

Strasser et al., "Improved virus neutralization by plant-produced anti-HIV antibodies with a homogeneous β1,4-galactosylated N-glycan profile," J. Biol. Chem., 2009, 284(31):20479-20485.

Su et al., "Engineered yeast with PNGase F on cell surface for releasing of N-glycans from glycoproteins," Enzyme Microbial Technol., Mar. 2007, 40(6):1496-1502.

Tarentino et al., "Molecular cloning and amino acid sequence of peptide-N4-(N-acetyl-beta-D-glucosaminyl)asparagine amidase from *Flavobacterium meningosepticum*," J. Biol. Chem., 1990, 265(12):6961-6966.

Tekoah et al., "Controlled glycosylation of therapeutic antibodies in plants," Archives Biochem. Biophysics, Jun. 2004, 426(2):266-278.

Verma et al., "A protocol for expression of foreign genes in chloroplasts," Nature Protocols, 2008, 3:739-758.

Vézina et al., "Transient co-expression for fast and high-yield production of antibodies with human-like N-glycans in plants," Plant Biotechnol. J., 2009, 7(5):442-455).

Voinnet et al., "An enhanced transient expression system in plants based on suppression of gene silencing by the p19 protein of tomato bushy stunt virus," Plant J., 2003, 33:949-956.

Xiang et al., "A 38-amino-acid sequence encompassing the arm domain of the cucumber necrosis virus coat protein functions as a chloroplast transit peptide in infected plants," J. Virol., 2006, 80(16):7952-64.

Xie et al., "Measurement of the functional affinity constant of a monoclonal antibody for cell surface receptors using kinetic exclusion fluorescence immunoassay," J. Immunol. Meth., 2005, 304:1-14.

Qingxiang et al., "Glycosyltransferases and the Enzymes of Deglycosylation," Amino Acids Biotic Res., Dec. 1997, 19(2):38-43 (English abstract on p. 6).

Canadian Intellectual Property Office, Examination Report for Canadian Appl. No. 2,839,932 dated Dec. 30, 2019, 3 pp.

Brazil Instituto Nacional Da Propriedade Industrial, Examination Report for Brazilian Appl. No. BR112013031564-4 dated May 28, 2021, 14 pp.

Dang, et al. "Breast cancer subtype-specific interactions with the microenvironment dictate mechanisms of invasion" Cancer Res. Nov. 1, 2011; 71(21): 6857-6866. doi:10.1158/0008-5472.CAN-11-1818.

Tretter, et al. "Peptide-N4-(N-acetyl-/3-glucosaminyl)asparagine amidase F cannot release glycans with fucose attached a1+3 to the asparagine-linked N-acetylglucosamine residue" Eur. J. Biochem. 299, 647-652 (1991).

Wescott, et al. "An epigenetically distinct breast cancer cell subpopulation promotes collective invasion" The Journal of Clinical Investigation, http://www.jci.org on Apr. 7, 2015. http://dx.doi.org/10.1172/JCI77767.

Wescott, et al. "DNp63-Regulated Epithelial-to-Mesenchymal Transition State Heterogeneity Confers a Leader-Follower Relationship That Drives Collective Invasion" Cancer Res; 80(18) Sep. 15, 2020, AACRJournals.org | 3933-3944.

\* cited by examiner

FIG. 1A

ATGGGTTCGTGCTGTTCTCTCAGCTTCCATCTTCCTTTGTGTCTCTGATTCTCAT
TCTTGCAGAGCTGCTCCAGCTGCTCCAATACACCGTGAACATTAAGACCTTCGATGTGATCTTCGGTTGAT
GGTCTTTCTCAATCTGCTGAGGGAACTTTTACCTTCCGTGATGTGACTGTTAAGACCATCAAGATGTTCA
TCAAGAACGAGTGCCTAACAAGAACTTGTGATGGGATAGTGGATACTCCTTAGATGAACTGAAGAACAAGACT
ACTGGTGATTGATGAGTGATTTCAAGTTCTGGGTTGCTACTCCTTACTGGAACTGAGAAGTTCCTAGAGGTCTTTG
AGATTGATGTGACCGATTGATGAGACGTATAACCGAATAATACCGAGAGTTACACCGAGACTTGTCTTGC
TAAGGTAGAGAGGTACTCCGTTGAATTCGATATTGTGTCCATTGATGGTCATACAAGTACTCTTGTTGTTCCT
GTGATCAGTAACAAGTATCCTATAACACGAGAAGGTAGTATCTTAGGATCAGCCACTATTTGGGTATGCGTAATGGA
ATTCAGTTGCCTAGGAGTGCGTTGTGCTAGTTGTGTTAACCCCATAACAACCAAGCTAACACTTTCCAG
TGCCTGGTCCTAGAGGTTGTCCTAGTGTCTGTTCTGCTAAACCTAGATTGATGTCTAACAATCTCCGTTCTAACTCAG
CATCAGTTGGTGTCTGTTATGGCCTGTATGGCCTGTATGGCTGTTCTGTTCTAGGACTAACAACGGTGATGCTATCACCGTTCTAAATTAGCTCTTTGTGA
CTGGTTGGTGTCTGTTATGGCCTGTATGGCTGTTCTGTTCTAGGACTAACAACGGTGATGCTATCACCGTTCTAAATTAGCTCTTTGTGA
TCGCTAAGTCTAATACCCTATTTCGCTCCTGGTGACAATGATTACAAGGATGATAAGGATGAGGCTT
TAG (SEQ ID NO:1)

FIG. 1B

MGFVLRSQLPSFLLVSTILFLVISHSCRAAPADNTVNIKTFDKVFNAFGDGLSQSAEGITFPADVTTVKTKMFIK
NECPNKTCEWDRYANVYVENKTGEWYEIGRFITPYWVGTEKLPRGLEIDVTDFKSLLSGNTELKITETCLAKGR
EYSVDFDIVVGTPDYKYSAVVPVIQYNKSIDGVPYGRAHTLGLKKNIQLPTNTEKAYLRTTISGWGHAKPYDAGSRG
CAEWCFRHTLAINFANTFQEHQLGALGCSANPINNQSPGNWAPDRAGWCPGMAVPTRIDVLNNSLTGSTFSYEYKFQ
SWTNNGTINGDAFYAISSPVLAKSNTTSAPVVTNDYKDDDDKEL (SEQ ID NO:2)

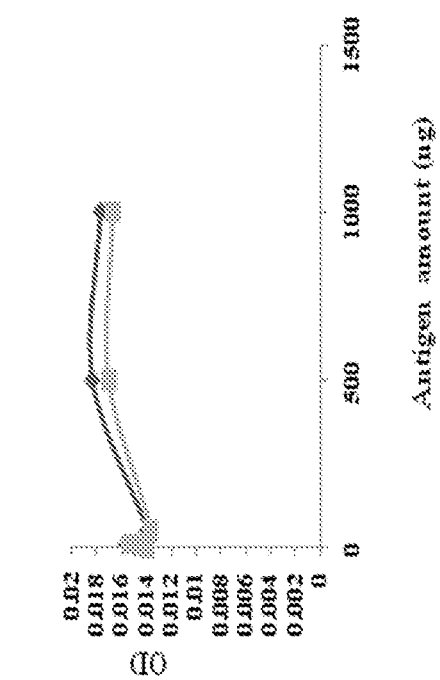
FIG. 5A mAb I
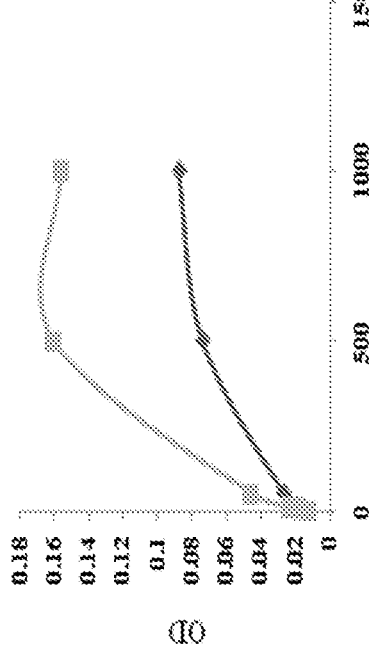
FIG. 5B mAb IIb
FIG. 5C mAb III
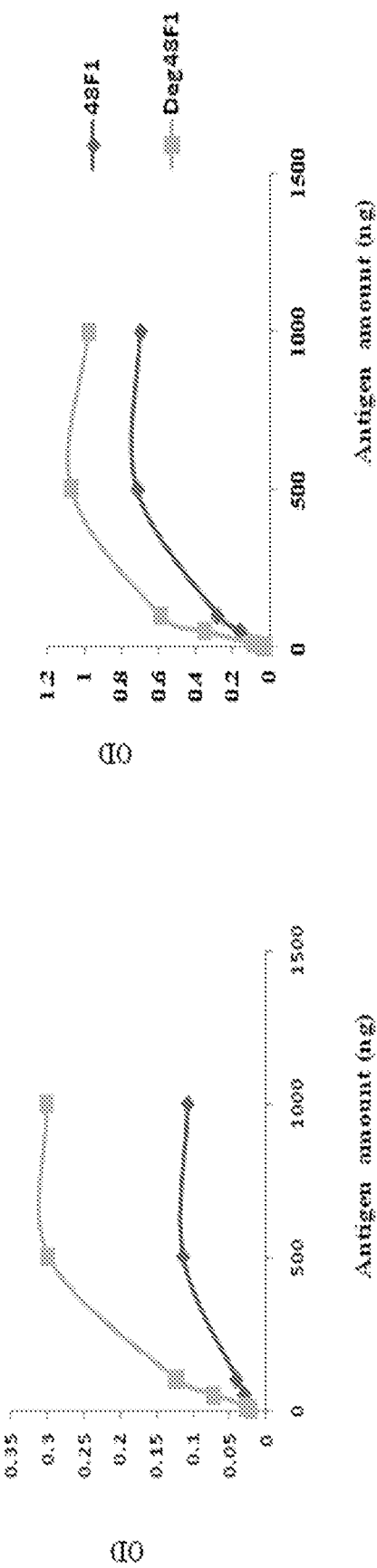
FIG. 5D mAb V

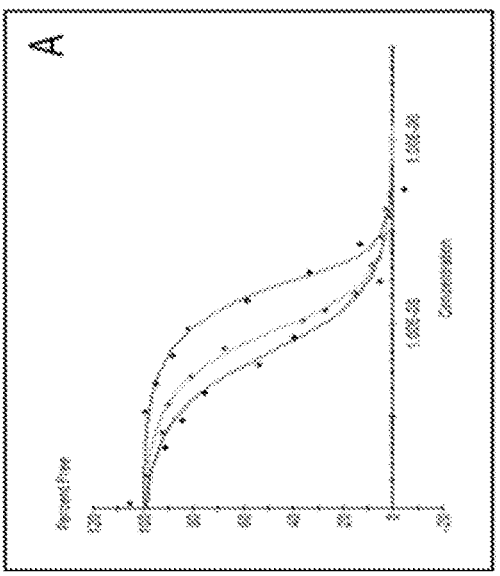
FIG. 6A
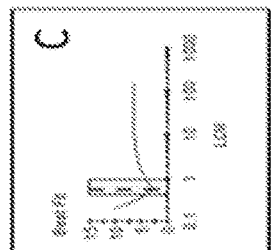
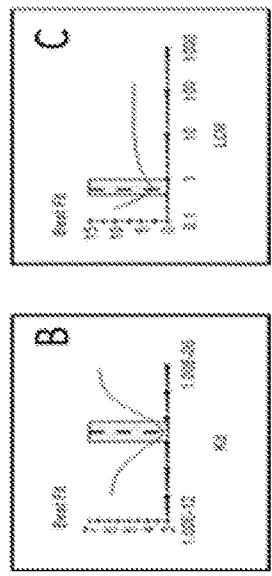
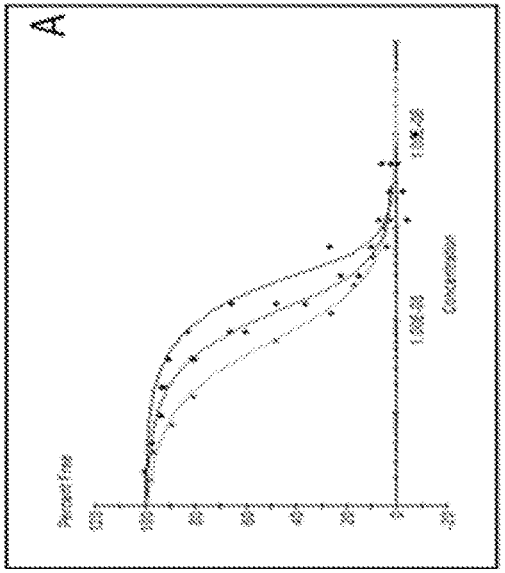
FIG. 6B
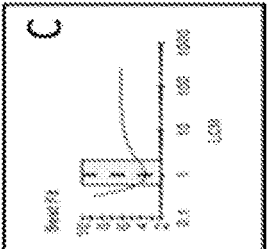
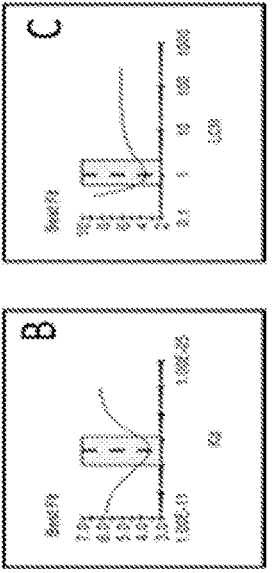
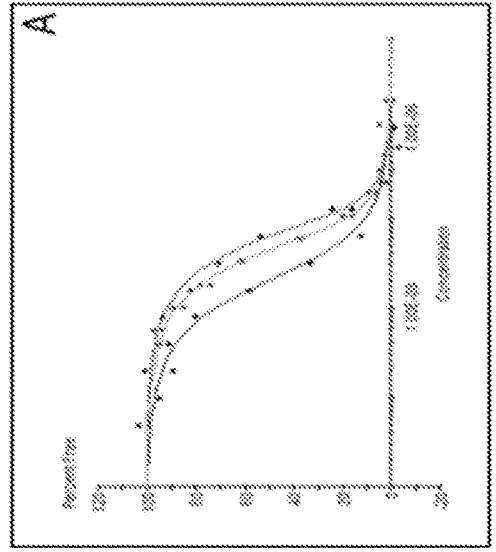
FIG. 6C
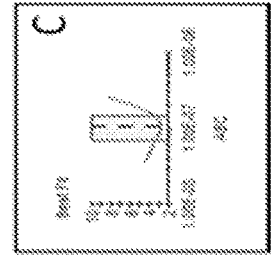
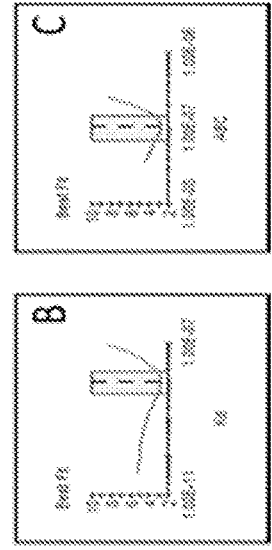
Kd (nM): 11.48    4.76    2.57

IN VIVO DE-GLYCOSYLATION OF RECOMBINANT PROTEINS BY CO-EXPRESSION WITH PNGASE F

CROSS-REFERENCE TO RELATED APPLICATIONS

This application is a National Stage application under 35 U.S.C. § 371 of International Application No. PCT/US2012/041340 having an International Filing Date of Jun. 7, 2012, which claims the benefit of priority of U.S. Provisional Application Serial No. 61/564,427, filed on Nov. 29, 2011, and U.S. Provisional Application Serial No. 61/494,141, filed on Jun. 7, 2011.

TECHNICAL FIELD

This document relates to materials and methods for producing recombinant proteins of interest in plants in a non-glycosylated form.

BACKGROUND

Plant-based expression has been investigated as a method for producing recombinant pharmaceutical proteins. The technology can be particularly useful for expressing glycosylated proteins. Mammalian glycoproteins, for example, are efficiently glycosylated when they are expressed in transgenic plants.

However, the ability of plants to glycosylate proteins also can be a significant limitation on the usefulness of plant-based expression systems. Some eukaryotes (e.g., *Plasmodium* parasites), for example, lack machinery for N-linked glycosylation. Proteins native to such species may contain multiple potential glycosylation sites that could be aberrantly glycosylated when expressed in plants, leading to reduced functionality and immunogenicity due to incorrect/altered folding or masking of epitopes, for example. Indeed, the attachment of carbohydrate can strongly affect the physico-chemical properties of a protein, and therefore can alter essential biological functions such as immunogenicity, specific activity, and ligand-receptor interactions of the protein.

Aberrant N-glycosylation poses problems for many therapeutic applications. For example, cancer cells frequently are characterized by aberrant increases in protein N-glycosylation (Mihai et al. (2009) *Cancer Res.* 69:5673). In addition, aberrant N-glycosylation of cell surface receptors, including integrins and cadherins, appears to be associated with changes in carcinoma progression and metastasis (Guo et al. (2002) *Cancer Res.* 62:6837-6845; Partridge et al. (2004) *Science* 306:120-124; and Isaji et al. (2004) *J. Biol. Chem.* 279:19747-19754). Moreover, there are major structural differences between plant and mammalian N-linked glycans. For example, plant complex N-glycans contain β1,2-xylose and α1,3-fucose residues that are not present in human complex glycans. In addition, it should be noted that due to different glycosylation stages, recombinant proteins can be produced in multiple forms when they are expressed in transgenic plants, thus creating additional work to separate those forms during protein purification.

Efforts have been made to humanize N-linked glycosylation and N-glycans of biopharmaceuticals expressed in plants (Bakker et al. (supra); Saint-Jore-Dupas et al. (2007) *Trends Biotechnol.* 25(7):317-323; Frey et al. (2009) *Plant Biotechnol. J.* 7(1):33-48; Matsuo and Matsumura (2011) *Plant Biotechnol. J.* 9(2):264-281; Misaki et al. (2003) *Glycobiol.* 13(3):199-205; Palacpac et al. (1999) *Proc. Natl. Acad. Sci. USA* 96(8):4692-4697; Strasser et al. (2009) *J. Biol. Chem.* 284(31):20479-20485; and Vézina et al. (2009) *Plant Biotechnol. J.* 7(5):442-455).

Enzymatic de-glycosylation of proteins in vivo has not been satisfactorily achieved previously in any eukaryotic system, however, including in plant systems. For example, strategies such as the use of tunicamycin to block N-glycosylation resulted in a non-uniform expression of proteins in plants (Hori and Elbein (1981) *Plant Physiol.* 67:882-886; and Frank et al. (2008) *Plant Physiol.* 148(3):1354-1367).

SUMMARY

This document provides materials and methods for producing de-glycosylated forms of proteins (e.g., particular vaccine candidates or therapeutic proteins) in plant cells using transient expression methods. Proteins produced using such methods can be especially useful for their functionality and immunogenicity.

This document is based in part on the development of methods for producing de-glycosylated proteins in plant cells, by transiently expressing bacterial Peptide: N-glycosidase F (PNGase F) in a cell, in combination with another polypeptide of interest. Bacterial PNGase F has not previously been expressed in plant systems. As described in the Examples below, bacterial PNGase F was transiently co-expressed with several recombinant proteins (specifically, malaria vaccine candidate Pfs48F1E, *B. anthracis* protective antigen (PA), and an antibody against *B. anthracis* PA) in *N. benthamiana*. The bacterial PNGase F was fully active in vivo and successfully cleaved N-linked oligosaccharides from the target glycoproteins, resulting in uniformity of the expressed proteins.

Thus, the studies described herein demonstrate that enzymatic de-glycosylation of proteins can be achieved in vivo using an introduced de-glycosylation enzyme in a eukaryotic system. This strategy can be used to produce therapeutic proteins and antibodies in de-glycosylated forms in a transient plant expression system. This can be very important for some proteins, especially those that are not glycosylated in their native host but may be aberrantly glycosylated when expressed in other eukaryotic hosts, potentially leading to reduced functionality and immunogenicity. The methods provided herein may have broad applications in modifying many targets (e.g., proteins, antibodies, vaccine candidates) in plants such as *N. benthamiana* by co-expressing these targets with modifying enzymes such as PNGase F.

In one aspect, this document features a method for generating a de-glycosylated polypeptide of interest. The method can include producing a eukaryotic cell that comprises (a) a first nucleic acid comprising a first nucleotide sequence encoding a bacterial PNGase F polypeptide, wherein the first nucleotide sequence is operably linked to a promoter such that when the promoter is activated, the PNGase F polypeptide is expressed; and (b) a second nucleic acid comprising a nucleotide sequence encoding the polypeptide of interest, wherein the second nucleotide sequence is operably linked to a promoter such that when the promoter is activated, the polypeptide of interest is expressed, wherein by action of the PNGase F polypeptide, the polypeptide of interest is de-glycosylated. The method can include simultaneously introducing the first and second nucleic acids into the cell, separately introducing the first and second nucleic acids into the cell. The first and second nucleic acids can be present in the same nucleic acid construct. The eukaryotic cell can be a plant cell (e.g., a *Nicotiana benthamiana* cell).

The first nucleotide sequence can have at least 90 percent sequence identity to the sequence set forth in SEQ ID NO:1. The PNGase F polypeptide can have an amino acid sequence with at least 90 percent sequence identity to the sequence set forth in SEQ ID NO:2. The first and second nucleic acids can be introduced into the cell via an *Agrobacterium* construct.

In another aspect, this document features a eukaryotic cell comprising (a) a first nucleic acid comprising a first nucleotide sequence encoding a bacterial PNGase F polypeptide, wherein the first nucleotide sequence is operably linked to a promoter such that when the promoter is activated, the PNGase F polypeptide is expressed; and (b) a second nucleic acid comprising a nucleotide sequence encoding the polypeptide of interest, wherein the second nucleotide sequence is operably linked to a promoter such that when the promoter is activated, the polypeptide of interest is expressed. The eukaryotic cell can be a plant cell (e.g., a *Nicotiana benthamiana* cell). The first nucleotide sequence can have at least 90 percent sequence identity to the sequence set forth in SEQ ID NO:1. The PNGase F polypeptide can have an amino acid sequence with at least 90 percent sequence identity to the sequence set forth in SEQ ID NO:2.

This document also features a method for expressing an active bacterial PNGase F polypeptide in a plant cell, comprising introducing into the plant cell a nucleic acid comprising a nucleotide sequence encoding the bacterial PNGase F polypeptide, wherein the nucleotide sequence is operably linked to a promoter such that when the promoter is activated, the PNGase F polypeptide is expressed. The nucleotide sequence can have at least 90 percent sequence identity to the sequence set forth in SEQ ID NO:1. The PNGase F polypeptide can have an amino acid sequence with at least 90 percent sequence identity to the sequence set forth in SEQ ID NO:2. The nucleic acid can be introduced into the plant cell via an *Agrobacterium* construct. The plant cell can be a *Nicotiana benthamiana* cell.

In another aspect, this document features an expression system comprising (a) a first nucleic acid comprising a first nucleotide sequence encoding a bacterial PNGase F polypeptide, wherein the first nucleotide sequence is operably linked to a promoter such that when the first nucleic acid is introduced into a eukaryotic cell and the promoter is activated, the PNGase F polypeptide is expressed; and (b) a second nucleic acid comprising a nucleotide sequence encoding a polypeptide of interest, wherein the second nucleotide sequence is operably linked to a promoter such that when the second nucleic acid is introduced into the eukaryotic cell and the promoter is activated, the polypeptide of interest is expressed. The first nucleotide sequence can have at least 90 percent sequence identity to the sequence set forth in SEQ ID NO:1. The PNGase F polypeptide can have an amino acid sequence with at least 90 percent sequence identity to the sequence set forth in SEQ ID NO:2, and wherein the polypeptide retains glycosidase activity. The eukaryotic cell can be a plant cell (e.g., a *Nicotiana benthamiana* cell).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows the nucleotide and amino acid sequences of PNGase F that were expressed in *Nicotiana benthamiana* as described herein. FIG. 1A shows the nucleotide sequence (SEQ ID NO:1) of the PNGase F gene from *Elizabethkingia meningoseptica* (GENBANK® Accession no. J05411) as codon optimized for expression in *N. benthamiana* fused with nucleotides encoding FLAG tag and KDEL (SEQ ID NO:5). FIG. 1B shows the deduced amino acid sequence (SEQ ID NO:2) of PNGase F. MGFVLFSQLPSFLL-VSTLLLFLVISHSCRA (SEQ ID NO:3) is the tobacco PR-1a signal peptide; DYKDDDDK (SEQ ID NO:4) is the FLAG epitope.

FIG. 5 illustrates results obtained from a comparative ELISA analysis of glycosylated (diamonds) and deglycosylated (squares) forms of Pfs48F1. Monoclonal antibodies that recognize epitopes I (FIG. 5A), IIb (FIG. 5B), III (FIG. 5C), and V (FIG. 5D) of Pfs48F1 were used in the analysis.

FIG. 6 illustrates affinity of mAb V binding to Pfs48F1 variants. Kinetic assays were conducted as explained in Example 1 using purified Pfs48F1 from transformed *N. benthamiana* (FIG. 6A), purified Pfs48F1 de-glycosylated with PNGase F in vitro (FIG. 6B), and in vivo de-glycosylated Pfs48F1 purified from transformed *N. benthamiana* co-expressing PNGase F (FIG. 6C). In vivo deglycosylation of Pfs48F1 and purification of in vivo deglycosylated Pfs48F1 were performed as described in the Examples herein.

DETAILED DESCRIPTION

Figures 2A, 2B:
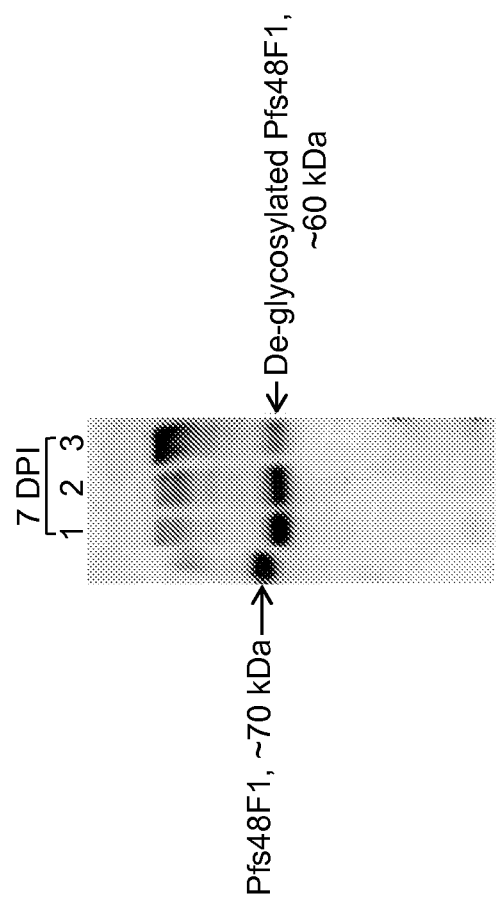
FIG. 2 shows Western blots of extracts from *N. benthamiana* leaves co-expressing Pfs48F1 and bacterial PNGase F. Leaf samples were taken at 5 DPI (days post infiltration), 6 DPI, and 7 DPI, and were ground in extraction buffer for TSP (total soluble protein), extraction buffer with Triton X-100 for TSPT (TSP extracted with 0.5% Triton X-100), and extraction buffer with 1× sodium dodecyl sulfate (SDS) sample buffer for TP (total protein). PNGase F (FIG. 2A) was detected with anti-FLAG polyclonal antibody; Pfs48F1E (FIG. 2B) was detected with mouse monoclonal anti-His antibody. 1, TP; 2, TSP; 3, TSPT.

The materials and methods described herein can be used to produce de-glycosylated forms of proteins (e.g., vaccine candidates and therapeutic proteins) in plants (e.g., *N. benthamiana*). Proteins produced using such methods can be especially useful for their functionality and immunogenicity.

Definitions

Nucleic acid: The terms "nucleic acid," "polynucleotide," and "oligonucleotide" are used interchangeably herein to refer to a polymer of at least three nucleotides. A nucleoside comprises a nitrogenous base linked to a sugar molecule. In a polynucleotide, phosphate groups covalently link adjacent nucleosides to form a polymer. The polymer can include natural nucleosides (e.g., adenosine, thymidine, guanosine, cytidine, uridine, deoxyadenosine, deoxythymidine, deoxyguanosine, and deoxycytidine), nucleoside analogs, chemically modified bases, biologically modified bases (e.g., methylated bases), intercalated bases, and/or modified sugars (e.g., modified purines or pyrimidines). See, Kornberg and Baker (1992) *DNA Replication*, 2nd Ed., Freeman, San Francisco, Calif.; Scheit (1980) *Nucleotide Analogs*, John Wiley, New York, N.Y.), and U.S. Patent Publication No. 20040092470 and references therein for further discussion of various nucleotides, nucleosides, and backbone structures that can be used in the polynucleotides described herein. A polynucleotide can have any length and sequence, and can be single-stranded or double-stranded. Where this document provides a nucleic acid sequence, the complementary sequence also is provided. Further, where a sequence is provided as DNA, the corresponding RNA sequence (i.e., the sequence in which T is replaced by U) also is provided.

Nucleic acid construct: The term "nucleic acid construct" is used herein to refer to a nucleic acid that has been modified by the hand of man or is derived from such a nucleic acid. For example, a nucleic acid construct can contain a mutation, deletion, or substitution relative to a naturally occurring nucleic acid molecule. A nucleic acid construct can comprise two or more nucleic acid segments that are derived from or originate from different sources such as different organisms (e.g., a recombinant polynucleotide). The sequence of one or more portions of a nucleic acid construct may be entirely invented by man.

Nucleic acid sequence: The term "nucleic acid sequence" as used herein refers to the nucleic acid material itself, and is not restricted to the sequence information (i.e., the succession of letters chosen among the five base letters A, G, C, T, or U) that biochemically characterizes a specific nucleic acid (e.g., DNA or RNA) molecule.

Gene: For the purposes of this document, the term "gene" has its meaning as understood in the art. In general, the term "gene" refers to a nucleic acid that includes a portion encoding a protein; the term optionally may encompass regulatory sequences such as promoters, enhancers, terminators, etc., in addition to coding sequences (open reading frames). This definition is not intended to exclude application of the term "gene" to non-protein coding expression units but rather to clarify that, in most cases, the term as used in this document refers to a protein-encoding nucleic acid. It will be appreciated that the definition of gene can include nucleic acids that do not encode proteins, but rather provide templates for transcription of functional RNA molecules such as tRNAs or rRNAs, for example.

Gene product or expression product: A gene product or expression product is, in general, an RNA transcribed from the gene or a polypeptide encoded by an RNA transcribed from the gene. Expression of a gene or a polynucleotide refers to (1) transcription of RNA from the gene or polynucleotide; (2) translation of RNA transcribed from the gene or polynucleotide, or both (1) and (2).

Vector: "Vector" refers to a nucleic acid or a virus, viral genome, or portion thereof (e.g., a viral capsid or a component of a viral genome) that is capable of mediating entry of (e.g., transferring or transporting) a nucleic acid molecule into a cell. Where the vector is a nucleic acid, the nucleic acid molecule to be transferred is generally linked to, e.g., inserted into, the vector nucleic acid molecule. A nucleic acid vector may include sequences that direct autonomous replication within suitable host cells (e.g., an origin of replication), or may include sequences sufficient to allow integration of part of all of the nucleic acid into host cell DNA. Useful nucleic acid vectors include, for example, DNA or RNA plasmids, cosmids, and naturally occurring or modified viral genomes or portions thereof, or nucleic acids (DNA or RNA) that can be packaged into viral capsids. Plasmid vectors typically include an origin of replication and one or more selectable markers. Plasmids may include part or all of a viral genome (e.g., a viral promoter, enhancer, processing or packaging signals, etc.). Viruses or portions thereof (e.g., viral capsids) that can be used to introduce nucleic acid molecules into cells are referred to as viral vectors. Useful animal viral vectors include adenoviruses, retroviruses, lentiviruses, *vaccinia* virus and other poxviruses, herpes simplex virus, and others. Useful plant viral vectors include those based on tobamoviruses, ilarviruses, etc. Viral vectors may or may not contain sufficient viral genetic information for production of infectious virus when introduced into host cells, i.e., viral vectors may be replication-defective, and such replication-defective viral vectors may be preferable for certain embodiments of the invention. Where sufficient information is lacking it may, but need not be, supplied by a host cell or by another vector introduced into the cell. An "expression vector" is a vector that includes one or more expression control sequences, and an "expression control sequence" is a DNA sequence that controls and regulates the transcription and/or translation of another DNA sequence.

Polynucleotide of interest: As used herein, the term "polynucleotide of interest" refers to any target sequence to be expressed a cell, as described herein. A polynucleotide of interest can be, for example, a protein-coding polynucleotide, but also may be a sequence that provides a template for transcription of a structural RNA or an active RNA such as, e.g., a ribozyme or interfering RNA. In some embodiments, a polynucleotide can be a gene that is not expressed in nature in the relevant type of cell, or is not expressed at the level that the polynucleotide is expressed when expression is achieved by intervention of the hand of man, as described herein. In certain embodiments, a polynucleotide of interest can include sequences that are not naturally found in the relevant cell, but are found naturally in other cell types or organisms. Alternatively or additionally, a polynucleotide of interest can be one that is not naturally associated with the vector sequences with which it is associated according to the present document.

Operably linked: As used herein, the term "operably linked" refers to a relationship between two nucleic acid sequences wherein the expression of one of the nucleic acid sequences is, e.g., controlled by, regulated by, or modulated by the other nucleic acid sequence. For example, transcription of a nucleic acid sequence is directed by an operably linked promoter sequence; post-transcriptional processing of a nucleic acid is directed by an operably linked processing sequence; translation of a nucleic acid sequence is directed by an operably linked translational regulatory sequence; transport or localization of a nucleic acid or polypeptide is directed by an operably linked transport or localization sequence; and post-translational processing of a polypeptide is directed by an operably linked processing sequence. A nucleic acid sequence that is operably linked to a second nucleic acid sequence typically is covalently linked, either directly or indirectly, to such a sequence, although any effective three-dimensional association is acceptable. It is noted that a single nucleic acid sequence can be operably linked to a plurality of other sequences. For example, a single promoter can direct transcription of multiple RNA species. A coding sequence is "operably linked" and "under the control" of an expression control sequence in a cell when RNA polymerase is able to transcribe the coding sequence into mRNA, which then can be translated into the protein encoded by the coding sequence.

Host cell: The term "host cell" includes cells into which a recombinant expression vector can be introduced. A host cell for use with the disclosed expression systems and methods typically is a eukaryotic cell, such as a plant cell. As used herein, "transformed" and "transfected" encompass the introduction of a nucleic acid molecule (e.g., a vector) into a cell by one of a number of techniques.

Polypeptide: As used herein, the terms "polypeptide" refers to an amino acid chain, regardless of length or post-translational modification (e.g., glycosylation or phosphorylation). Polypeptides can include full length proteins or fragments or variants thereof. A "polypeptide of interest" refers to a target sequence expressed a cell, as described herein. In some embodiments, a polypeptide of interest can be a polypeptide that is not expressed in nature in the relevant type of cell, or is not expressed at the level that the polypeptide is expressed when expression is achieved by intervention of the hand of man, as described herein. In certain embodiments, a polypeptide of interest can include sequences that are not naturally found in the relevant cell, but are found naturally in other cell types or organisms.

Percent Identity: "Identity" refers to the extent to which two or more nucleic acid sequences or two or more amino acid sequences are the same. The percent identity between two sequences over a window of evaluation is computed by aligning the sequences, determining the number of nucleotides or amino acids within the window of evaluation that are opposite an identical nucleotide or amino acid, allowing the introduction of gaps to maximize identity, dividing by the total number of nucleotides or amino acids in the window, and multiplying by 100.

Percent identity for any nucleic acid or amino acid sequence is determined as follows. First, a nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (World Wide Web at fr.com/blast) or the U.S. government's National Center for Biotechnology Information web site (World Wide Web at ncbi.nlm.nih.gov/blast/executables). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: −i is set to a file containing the first nucleic acid sequence to be compared (e.g., C:\seq1.txt); −j is set to a file containing the second nucleic acid sequence to be compared (e.g., C:\seq2.txt); −p is set to blastn; −o is set to any desired file name (e.g., C:\output.txt); −q is set to −1; −r is set to 2; and all other options are left at their default setting. For example, the following command can be used to generate an output file containing a comparison between two sequences: C:\Bl2seq c:\seq1.txt −j c:\seq2.txt −p blastn −o c:\output.txt −q −1 −r 2. To compare two amino acid sequences, the options of Bl2seq are set as follows: −i is set to a file containing the first amino acid sequence to be compared (e.g., C:\seq1.txt); −j is set to a file containing the second amino acid sequence to be compared (e.g., C:\seq2.txt); −p is set to blastp; −o is set to any desired file name (e.g., C:\output.txt); and all other options are left at their default setting. For example, the following command can be used to generate an output file containing a comparison between two amino acid sequences: C:\Bl2seq c:\seq1.txt −j c:\seq2.txt −p blastp −o c:\output.txt. If the target sequence shares homology with any portion of the identified sequence, then the designated output file will present those regions of homology as aligned sequences. If the target sequence does not share homology with any portion of the identified sequence, then the designated output file will not present aligned sequences. Once aligned, a length is determined by counting the number of consecutive nucleotides or amino acid residues from the target sequence presented in alignment with sequence from the identified sequence starting with any matched position and ending with any other matched position. A matched position is any position where an identical nucleotide or amino acid residue is presented in both the target and identified sequence. Gaps presented in the target sequence are not counted since gaps are not nucleotides or amino acid residues. Likewise, gaps presented in the identified sequence are not counted since target sequence nucleotides or amino acid residues are counted, not nucleotides or amino acid residues from the identified sequence.

The percent identity over a determined length is determined by counting the number of matched positions over that length and dividing that number by the length followed by multiplying the resulting value by 100. For example, if (1) a 1000 nucleotide target sequence is compared to the sequence set forth in SEQ ID NO:1, (2) the Bl2seq program presents 200 nucleotides from the target sequence aligned with a region of the sequence set forth in SEQ ID NO:1 where the first and last nucleotides of that 200 nucleotide region are matches, and (3) the number of matches over those 200 aligned nucleotides is 180, then the 1000 nucleotide target sequence contains a length of 200 and a percent identity over that length of 90 (i.e., (180÷200)*100=90).

It will be appreciated that a single nucleic acid or amino acid target sequence that aligns with an identified sequence can have many different lengths with each length having its own percent identity. In addition, it is noted that the percent identity value is rounded to the nearest tenth. For example, 78.11, 78.12, 78.13, and 78.14 is rounded down to 78.1, while 78.15, 78.16, 78.17, 78.18, and 78.19 are rounded up to 78.2. It is also noted that the length value will always be an integer.

Isolated: As used herein, the term "isolated" refers to a compound or entity that is (a) separated from at least some of the components with which it is normally associated (e.g., purified); (b) synthesized in vitro; and/or (c) produced or prepared by a process that involves the hand of man.

Naturally: The terms "naturally" and "naturally-occurring," as used herein, refer to processes, events, or things that occur in their relevant form in nature. In contrast, the term "not-naturally-occurring" refers to processes, events, or things whose existence or form involves the hand of man.

De-glycosylated: The term "de-glycosylated," as used herein with respect to polypeptides produced in the presence of or otherwise exposed to a PNGase F polypeptide, refers to polypeptides that have a lesser degree of N-linked glycosylation than they would if they were not produced in the presence of or otherwise exposed to the PNGase F polypeptide. "De-glycosylated" polypeptides can have a level of N-linked glycosylation that is reduced by at least about 10 percent (e.g., 10 percent, 20 percent, 30 percent, 40 percent, 50 percent, 60 percent, 70 percent, 80 percent, 90 percent, or 100 percent) as compared to the level of N-linked glycosylation of the same polypeptides that are not produced in the presence of or otherwise exposed to a PNGase F polypeptide.

Nucleic Acids and Vectors

The teachings provided herein can be used to deliver to and/or express in a cell (e.g., a plant cell) any polynucleotide of interest. Protein-encoding polynucleotides can express, for example, enzymes, antibodies, hormones, cytokines, regulatory factors, structural proteins, or any other protein or polypeptide of interest. Encoded proteins can be naturally-occurring proteins, or can be designed or engineered proteins including, for example, fusion proteins (e.g., fusion proteins incorporating part or all of a plant virus protein such as movement protein or coat protein). In some embodiments, the polynucleotide of interest can contain a portion encoding a tag, e.g., a 6X-His tag, HA tag, Myc tag, or FLAG tag. Such tags can simplify the isolation and/or purification of the protein. In some embodiments, the tag can be a cleavable tag (e.g., a tag cleavable by a protease such as thrombin), so that the tag can readily be removed after purification, resulting in a protein with wild type sequence.

In some embodiments, a polynucleotide can encode a therapeutically active protein. Exemplary proteins include, without limitation, hormones (e.g., insulin, thyroid hormone, catecholamines, gonadotropins, trophic hormones, prolactin, oxytocin, dopamine, bovine somatotropin, calcitonin, follicle stimulating hormone, and leptins), growth hormones (e.g., human grown hormone), growth factors (e.g., epidermal growth factor, nerve growth factor, platelet-derived growth factor, insulin-like growth factor, and the like), growth factor receptors, cytokines and immune system proteins [e.g., interleukins, colony stimulating factor (CSF), granulocyte colony stimulating factor (G-CSF), granulocyte-macrophage colony stimulating factor (GM-CSF), erythropoietin, tumor necrosis factor (TNF), TNF receptor (soluble form), interferons, integrins, addressins, selectins, homing receptors, T cell receptors, immunoglobulins, soluble major histocompatibility complex antigens, immunologically active antigens such as bacterial, parasitic, or viral antigens or allergens, autoantigens, and antibodies], enzymes (e.g., tissue plasminogen activator, streptokinase, cholesterol biosynthetic or degradative, steriodogenic enzymes, kinases, DNAses, phosphodiesterases, methylases, de-methylases, dehydrogenases, cellulases, proteases, lipases, phospholipases, aromatases, cytochromes, adenylate or guanylate cyclases, neuraminidases, and the like), receptors (e.g., steroid hormone receptors and peptide receptors), binding proteins (e.g., steroid binding proteins, growth hormone or growth factor binding proteins, and the like), transcription and translation factors, oncoproteins or proto-oncoproteins (e.g., cell cycle proteins), muscle proteins (e.g., myosin, tropomyosin, and the like), myeloproteins, neuroactive proteins, tumor growth suppressing proteins (e.g., angiostatin or endostatin, both of which inhibit angiogenesis), anti-sepsis proteins (e.g., bactericidal permeability-increasing protein), structural proteins (e.g., collagen, fibroin, fibrinogen, elastin, tubulin, actin, and myosin), and blood proteins (e.g., thrombin, serum albumin, Factor VII, Factor VIII, insulin, Factor IX, Factor X, tissue plasminogen activator, Protein C, von Willebrand factor, antithrombin III, glucocerebrosidase, erythropoietin granulocyte colony stimulating factor (GCSF) or modified Factor VIII, anticoagulants such as huridin, and the like). Of course, this document is not limited to proteins approved for therapeutic use, but also encompasses expression of any polynucleotide(s), whether protein-coding or not, and particularly encompasses expression of any polynucleotide encoding any therapeutically active protein, whether prokaryotic or eukaryotic in origin.

In some embodiments, a polynucleotide can encode one or more vaccine components. In general, it can be desirable for a vaccine to include proteins, or portions of proteins, to which a human or animal immune system is exposed when the human or animal is infected with a pathogen or suffering some other undesirable event (e.g., development of a tumor). Proteins and polypeptides that can be formulated into a vaccine include, without limitation, viral coat proteins, viral G proteins, microbial cell wall proteins, microbial toxin proteins, and tumor-specific antigens.

In some embodiments, a polynucleotide can be used to express an enzyme that synthesizes or modifies a biologically active agent. For example, certain enzymes (e.g., polyketide synthases, polypeptide synthetases, and terpene synthases) synthesize small molecules with interesting biological activities, including therapeutic activities (e.g., antibiotic, anticancer, or immunosuppressive activities). In addition, a large number of enzymes that modify protein or small molecule substrates (e.g., kinases, hydrolases, and transferases) are known. See, e.g., U.S. Pat. No. 6,500,644 for additional proteins that can be expressed in plants using the expression systems described herein.

In some embodiments, a polynucleotide can encode a diagnostic or research reagent including, for example, an antibody. In still other embodiments, a polynucleotide can encode a nutritionally relevant protein. Such proteins include, for example, proteins that are found naturally in foods consumed by humans or domesticated animals (e.g., cats and dogs). Other examples include proteins having a balanced amino acid composition, e.g., proteins having a composition such as those used for total parenteral nutrition.

A polynucleotide as provided herein can encode a PNGase F polypeptide, or a fragment of a PNGase F polypeptide that retains glycosidase activity. PNGase F is a 34.8 kDa enzyme secreted by the gram-negative bacterium, *Flavobacterium meningosepticum* (Plummer et al. (1984) *J. Biol. Chem.* 259(17):10700-10704; and Tarentino et al. (1990) *J. Biol. Chem.* 265(12):6961-6966). PNGase F cleaves a bond between the innermost GlcNAc and asparagine residues of high mannose, hybrid and complex oligosaccharides in N-linked glycoproteins unless the $\alpha(1-3)$ core is fucosylated. Typically, the PNGase F polynucleotides described herein encode a functional PNGase F polypeptide, or a fragment thereof, that can provide de-glycosylating activity when expressed in a cell. Methods for determining whether a PNGase F polypeptide or fragment has glycosidase activity include those known in the art. For example, the glycosidase activity of a PNGase F polypeptide can be tested in vitro and in vivo as described in Example 1 below. Typically, a PNGase F polypeptide fragment as provided herein can retain glycosidase activity to a level that is at least 10 percent (e.g., at least 10 percent, at least 20 percent, at least 25 percent, at least 30 percent, at least 40 percent, at least 50 percent, at least 60 percent, at least 70 percent, at least 75 percent, at least 80 percent, or at least 90 percent) of the level of glycosidase activity of a PNGase F polypeptide having the amino acid sequence set forth in SEQ ID NO:2.

Vectors containing nucleic acids such as those described herein also are provided. In the expression vectors provided herein, a nucleic acid (e.g., a nucleic acid encoding PNGase F or encoding a polypeptide of interest) can be operably linked to one or more expression control sequences. Examples of expression control sequences include promoters, enhancers, and transcription terminating regions. A promoter is an expression control sequence composed of a region of a DNA molecule, typically within 100 to 500 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site.

Suitable expression vectors include, without limitation, plasmids and viral vectors derived from, for example, bacteriophage, baculoviruses, tobacco mosaic virus and other plan viruses, herpes viruses, cytomegalovirus, retroviruses, *vaccinia* viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

An expression vector can include a tag sequence designed to facilitate subsequent manipulation and/or tracking of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

Polypeptides

The materials and methods described herein are applicable to the production of polypeptides, particularly de-glycosylated polypeptides, in eukaryotic cells (e.g., plant cells). As indicated above, in some embodiments, the polypeptides can be pharmaceutical proteins, although the methods generally are not limited by the particular use(s) of the polypeptides. For example, enzymes for use in any of a wide variety of industrial processes or bioremediation processes (e.g., enzymes that degrade pollutants) can be produced. Thus the description provided herein, and the claims, are to be considered as applying to any nucleic acid or protein of interest even if not explicitly indicated, including those with therapeutic applications and those without.

An expressed protein or polypeptide may or may not be one that is not expressed in the plant in nature. Non-limiting examples of polypeptides that can be expressed in a cell (e.g., a plant cell) according to the methods described herein include pharmaceutical proteins, such as hormones (e.g., insulin, thyroid hormone, catecholamines, gonadotropins, trophic hormones, prolactin, oxytocin, dopamine, bovine somatotropin, calcitonin, follicle stimulating hormone, and leptins), growth hormones (e.g., human grown hormone), growth factors (e.g., epidermal growth factor, nerve growth factor, insulin-like growth factor, platelet-derived growth factor, and the like), growth factor receptors, cytokines and immune system proteins (e.g., interleukins, CSF, G-CSF, GM-CSF, erythropoietin, TNF, TNF receptor (soluble form), interferons, integrins, addressins, selectins, homing receptors, T cell receptors, immunoglobulins, soluble major histocompatibility complex antigens, immunologically active antigens such as bacterial, parasitic, or viral antigens or allergens, autoantigens, and antibodies), enzymes (e.g., tissue plasminogen activator, streptokinase, cholesterol biosynthetic or degradative enzymes, steriodogenic enzymes, kinases, DNAses, phosphodiesterases, methylases, de-methylases, dehydrogenases, cellulases, proteases, lipases, phospholipases, aromatases, cytochromes, adenylate or guanylate cyclases, neuraminidases, and the like), receptors (steroid hormone receptors and peptide receptors), binding proteins (e.g., steroid binding proteins, growth hormone or growth factor binding proteins, and the like), transcription and translation factors, oncoproteins or proto-oncoproteins (e.g., cell cycle proteins), muscle proteins (e.g., myosin or tropomyosin and the like), myeloproteins, neuroactive proteins, tumor growth suppressing proteins (e.g., angiostatin or endostatin, both of which inhibit angiogenesis), anti-sepsis proteins (e.g., bactericidal permeability-increasing protein), structural proteins (such as collagen, fibroin, fibrinogen, elastin, tubulin, actin, and myosin), blood proteins e.g., (thrombin, serum albumin, Factor VII, Factor VIII, insulin, Factor IX, Factor X, tissue plasminogen activator, Protein C, von Wilebrand factor, antithrombin III, glucocerebrosidase, erythropoietin G-CSF, modified Factor VIII, and anticoagulants such as huridin), and the like.

In some embodiments, an expressed polypeptide can be an antigenic protein or polypeptide. For example, the methods described herein can be used to produce proteins (or portions thereof) of infectious organisms that are recognized by the immune system of an infected subject. Such proteins or polypeptides can be useful for developing vaccines for protection against infection by the relevant organisms. To give but a few specific examples, useful antigenic proteins from anthrax (e.g., *B. anthracis* lethal factor (LF) or PA), cholera (*Vibrio cholerae*), cytomegalovirus, enterotoxigenic strains of *E. coli*, foot-and-mouth disease virus, hepatitis B (e.g., hepatitis B surface antigen or HBsAg), hepatitis C (e.g., HCV core protein), human immunodeficiency virus (e.g., Tat, Rev, Nef, gp160, or gp120), human papilloma virus (e.g., E7 or E6), influenza (e.g., HA or NA), malaria (e.g., *Plasmodium falciparum* Pfs25, Pfs28, Pfs48/45, or Pfs230), measles virus, norwalk virus, plague (e.g., *Yersinia pestis* F1 or LcrV), *Pseudomonas aeruginosa*, rabies virus, respiratory syncytial virus (e.g., F protein or G protein), rhinovirus, rotavirus, *Staphylococcus aureus*, transmissible gastroenteritis virus, trypanosomes (e.g., *Trypanosoma brucei* alpha-tubulin or beta-tubulin), tuberculosis, or SARS can be produced in accordance with the presently described methods.

Expression Systems and Host Cells

This document also provides expression systems that can be used to produce de-glycosylated polypeptides in host cells (e.g., plant cells). The expression systems can include an expression vector that contains a polynucleotide sequence encoding a PNGase F polypeptide, as well as an expression vector containing a polynucleotide of interest that encodes a polypeptide or protein of interest. In some cases, the polynucleotide sequence encoding the PNGase F polypeptide and the polynucleotide of interest encoding the polypeptide or protein of interest can be included in the same nucleic acid construct. The polynucleotide sequences encoding the PNGase F polypeptide and the polypeptide or protein of interest each can be operably linked to a promoter, such that when the polynucleotides are introduced into a eukaryotic cell (e.g., an *N. benthamiana* cell) and the promoters are activated (e.g., conditionally or constitutively), the PNGase F polypeptide and the polypeptide or protein of interest are expressed. The promoters that are operably linked to the PNGase F coding sequence and the coding sequence for the polypeptide of interest may be the same or different. In some cases, the polynucleotide encoding the PNGase F polypeptide can have a sequence with at least 90 percent sequence identity (e.g., at least 91, 92, 93, 94, 95, 96, 97, 98, or 99 percent sequence identity, or 100 percent sequence identity) to the sequence set forth in SEQ ID NO:1. In some cases, the encoded PNGase F polypeptide can have an amino acid sequence with at least 90 percent sequence identity (e.g., at least 91, 92, 93, 94, 95, 96, 97, 98, or 99 percent sequence identity, or 100 percent sequence identity) to the sequence set forth in SEQ ID NO:2.

Any of a variety of different systems can be used to express proteins or polypeptides in plants, either through transient or stable transformation. Technologies for transiently expressing proteins or polypeptides in plant tissues can utilize, for example, plant viruses. Viral transformation can be a relatively rapid and low cost method of transforming embryos and plants that can be harvested without an experimental or generational lag prior to obtaining the desired product. On the other hand, viruses that are not attenuated can infect other plants, potentially causing environmental concerns.

In some embodiments, expression of a polypeptide of interest can be under the control of a constitutive promoter. In other embodiments, expression of a polypeptide of interest can be inducible, or can be under the control of a promoter that is tissue, timing, or developmentally regulated. In some cases, for example, production of an RNA encoding the polypeptide of interest can be under the control of an inducible (e.g., exogenously inducible) promoter. Exogenously inducible promoters can be used to increase or decrease expression of a transcript in response to an external, rather than an internal stimulus. A number of environmental factors can act as such external stimuli. In some embodiments, transcription can be controlled by a heat-inducible promoter such as a heat-shock promoter, for example.

Externally inducible promoters may be particularly useful in the context of controlled, regulatable growth settings. For example, using a heat-shock promoter the temperature of a contained environment may simply be raised to induce expression of the relevant transcript. In will be appreciated, of course, that a heat inducible promoter is not useful outdoors because the outdoor temperature cannot be controlled. Other externally-inducible promoters than can be used include light inducible promoters, which can be maintained as constitutive promoters if the light in the contained regulatable environment is always on. Alternatively, expression of a polypeptide of interest can be turned on at a particular time during development by simply turning on the light.

In other embodiments, a chemically inducible promoter can be used to induce expression of a polypeptide of interest. In such embodiments, the chemical could be misted or sprayed onto a seed, embryo, or plant to induce expression of the relevant polypeptide. Spraying and misting can be precisely controlled and directed onto a particular seed, embryo, or plant as desired. A contained environment is devoid of wind or air currents, which could disperse the chemical away from the intended recipient, so that the chemical stays on the recipient for which it was intended.

This document also provides expression systems having the advantages of viral expression systems (e.g., rapid expression, high levels of production) and of *Agrobacterium* transformation (e.g., controlled administration). For example, this document provides systems in which an Agrobacterial construct (i.e., a construct that replicates in *Agrobacterium* and therefore can be delivered to plant cells by delivery of *Agrobacterium*) includes a plant promoter that, after being introduced into a plant, directs expression of viral sequences (e.g., including viral replication sequences) carrying a gene for a protein or polypeptide of interest. This system allows controlled, high level transient expression of proteins or polypeptides in plants.

In some cases, a de-glycosylated polypeptide can be produced in a transgenic plant in which a PNGase F transgene and/or a transgene encoding a polypeptide of interest is stably integrated into the genomic DNA and is expressed (e.g., in cell nuclei). Methods for generating such plants are known in the art.

Host cells containing the nucleic acids and vectors described herein also are provided. A nucleic acid molecule (e.g., a vector) can be introduced into a host cell by one of a number of techniques including, without limitation, techniques that are well established within the art. For example, a nucleic acid can be introduced into a host cell by *Agro-* bacterium-based transformation (including vacuum-mediated transformation). See, e.g., the Examples below. Suitable methods for transforming and transfecting host cells also can be found, for example, in Sambrook et al., *Molecular Cloning: A Laboratory Manual* (2nd edition), Cold Spring Harbor Laboratory, New York (1989). These include, e.g., calcium phosphate precipitation, electroporation, heat shock, lipofection, microinjection, and viral-mediated nucleic acid transfer. In addition, naked DNA can be delivered directly to cells in vivo (see, e.g., U.S. Pat. Nos. 5,580,859 and 5,589,466).

Any plant susceptible to transient transfection can be utilized in accordance with the systems and methods provided herein. In general, it can be desirable to use plants that are amenable to growth under defined conditions, such as in a greenhouse and/or in aqueous systems. It also may be desirable to select plants that are not typically consumed by human beings or domesticated animals and/or are not typically part of the human food chain, so they can be grown outside without concern that the expressed polynucleotide might be undesirably ingested. In some embodiments, however, it may be desirable to use edible plants.

Desirable plant characteristics can be determined by the particular polynucleotide to be expressed. For example, when the polynucleotide encodes a protein to be produced in high yield (as may be the case, for example, when therapeutic proteins are to be expressed), it can be useful to select plants with relatively high biomass (e.g., tobacco, which also may be particularly useful for other reasons, such as having a short growth period and not being in the human food chain). In some embodiments, crop plants or crop-related plants can be used.

Plants that can be particularly useful with the expression systems and methods described herein include, without limitation, angiosperms (e.g., *Nicotiana*, including *N. benthamiana*), bryophytes (e.g., Hepaticae, Musci, etc.), pteridophytes (e.g., ferns, horsetails, and lycopods), gymnosperms (e.g., conifers, cycase, Ginko, Gnetales), and algae (e.g., Chlorophyceae, Phaeophyceae, Rhodophyceae, Myxophyceae, Xanthophyceae, and Euglenophyceae).

The systems and methods provided herein can be used to transfect and/or to express a polynucleotide in plants at any stage of development including, for example, mature plants, seedlings, sprouts, and seeds. The systems and methods can be used to transfect any part of a plant (e.g., roots, leaves, stems, etc.).

Methods

This document also provides methods for producing a de-glycosylated polypeptide of interest in a cell (e.g., a plant cell). In general, the methods can include delivering to a cell an expression vector encoding PNGase F, and an expression vector encoding the polypeptide of interest. For example, a method for producing a polypeptide of interest can include introducing into a eukaryotic cell (e.g., a plant cell, such as an *N. benthamiana* cell) a first nucleic acid encoding a bacterial PNGase F polypeptide, and a second nucleic acid encoding the polypeptide of interest. The nucleotide sequences within the first and second nucleic acids that encode the PNGase F polypeptide and the polypeptide of interest can be operably linked to promoters, such that when the promoters are activated (e.g., constitutively or conditionally), the PNGase F polypeptide and the polypeptide of interest are expressed, and by action of the PNGase F polypeptide, the polypeptide of interest is de-glycosylated. Methods for assessing the level of glycosylation include those known in the art (e.g., sodium dodecylsulfate-polyacrylamide gel electrophoresis (SDS-PAGE) and Western blotting analysis, as described in the Examples below, as well as mass spectrometry and glycan detection).

The promoters linked to the first and second nucleic acids may be the same or different promoters. Further, the first and second nucleic acids can be contained within separate constructs or within a single construct. In some embodiments, the nucleic acid encoding the PNGase F polypeptide can include a sequence with at least 90 percent sequence identity (e.g., at least 90, 91, 92, 93, 94, 95, 96, 97, 98, or 99 percent sequence identity, or 100 percent sequence identity) to the sequence set forth in SEQ ID NO:1. In some cases, the encoded PNGase F polypeptide can have an amino acid sequence with at least 90 percent sequence identity (e.g., at least 90, 91, 92, 93, 94, 95, 96, 97, 98, or 99 percent sequence identity, or 100 percent sequence identity) to the sequence set forth in SEQ ID NO:2.

Also provided herein are methods for expressing an active bacterial PNGase F polypeptide in a plant cell. The methods can include, for example, introducing into a plant cell (e.g., an *N. benthamiana* cell) a nucleic acid encoding a bacterial PNGase F polypeptide. The nucleic acid can include a nucleotide sequence that encodes the PNGase F polypeptide and that is operably linked to a promoter, such that when the nucleic acid is introduced into the plant cell, the PNGase F polypeptide is expressed. In some cases, the nucleic acid can include a sequence with at least 90 percent sequence identity (e.g., at least 90, 91, 92, 93, 94, 95, 96, 97, 98, or 99 percent sequence identity, or 100 percent sequence identity) to the sequence set forth in SEQ ID NO:1. In some embodiments, the encoded PNGase F polypeptide can have an amino acid sequence with at least 90 percent sequence identity (e.g., at least 90, 91, 92, 93, 94, 95, 96, 97, 98, or 99 percent sequence identity, or 100 percent sequence identity) to the sequence set forth in SEQ ID NO:2.

Expression vectors can be delivered to plants using techniques that are known in the art. For example, a vector can be directly applied to a plant (e.g., via abrasive inoculation, mechanized spray inoculation, vacuum infiltration, particle bombardment, or electroporation). Alternatively, virions can be prepared (e.g., from previously infected plants), and may be applied to other plants according to known techniques. The expression vectors can be introduced into the cell simultaneously or sequentially. When sequential introduction is used, any suitable length of time can pass between introduction of the first expression vector (typically the vector encoding PNGase F) and introduction of the second expression vector (typically the vector encoding the polypeptide of interest). For example, introduction of the first and second expression vectors can be separated by 1 to 60 minutes, 1 to 24 hours, or 1 to 30 days.

It is to be noted that in some embodiments, the first expression vector, the second expression vector, or both expression vectors can be stably transformed into plant cells, such that a transgenic line is generated. For example, if a plant is transgenic for PNGase F coding sequences, it can be transiently transformed with a vector encoding the polypeptide of interest, such that the expressed polypeptide of interest is de-glycosylated.

In some embodiments, *Agrobacterium* transformation can be used to introduce one or more expression constructs into a cell. *Agrobacterium* is a representative genus of the gram-negative family Rhizobiaceae. This species is responsible for plant tumors such as crown gall and hairy root disease. In de-differentiated plant tissue, which is characteristic of tumors, amino acid derivatives known as opines are produced by the *Agrobacterium* and catabolized by the plant. The bacterial genes responsible for expression of opines are a convenient source of control elements for chimeric expression cassettes. According to the methods described herein, the *Agrobacterium* transformation system can be used to generate plants that express a polypeptide of interest in de-glycosylated form.

*Agrobacterium* transformation methods can readily be applied to regenerate plants expressing pharmaceutical proteins. In general, transforming plants with *Agrobacterium* involves transformation of plant cells grown in tissue culture by co-cultivation with an *Agrobacterium tumefaciens* carrying a plant/bacterial vector containing, for example, a gene encoding a pharmaceutical protein. The *Agrobacterium* transfers the vector to the plant host cell and is then eliminated using antibiotic treatment. Transformed plant cells expressing the pharmaceutical protein can be selected, differentiated, and regenerated into complete plantlets (Hellens et al. (2000) *Plant Mol. Biol.* 42:819-832; Pilon-Smits et al. (1999) *Plant Physiolog.* 119(1):123-132; Barfield and Pua (1991) *Plant Cell Reports* 10(6/7):308-314; and de la Riva et al. (1998) *Electronic J. Biotechnol.* 1(3): online version ISSN 0717-3458).

Agrobacterial expression vectors can include a gene (or expression cassette) encoding a pharmaceutical protein designed for operation in plants, with companion sequences upstream and downstream of the expression cassette. The companion sequences generally are of plasmid or viral origin and provide necessary characteristics to the vector to transfer DNA from bacteria to the desired plant host. The basic bacterial/plant vector construct can provide a broad host range prokaryote replication origin, and a prokaryote selectable marker. Suitable prokaryotic selectable markers include, for example, markers that confer resistance to antibiotics such as ampicillin or tetracycline. Other DNA sequences encoding additional functions that are well known in the art may also be present in the vector. For example, if expression of the polypeptide of interest is not readily amenable to detection, the bacterial/plant vector construct also can include a selectable marker gene suitable for determining whether a plant cell has been transformed (e.g., the nptll kanamycin resistance gene).

Certain vectors can include the nucleic acid encoding the protein of interest. One, two, or more expression vectors may be used in a given transformation. The recombinant expression vector can contain at least the following elements in addition to the protein-encoding sequence: a promoter region, plant 5' untranslated sequences, initiation codon (depending upon whether or not the expressed gene has its own), and transcription and translation termination sequences. In addition, transcription and translation terminators and/or signal secretion sequences that allow processing and translocation of the protein can be included. A variety of promoters, signal sequences, and transcription and translation terminators are described, for example, in Lawton et al. (1987) *Plant Mol. Biol.* 9:315-324, and in U.S. Pat. No. 5,888,789. In addition, structural genes for antibiotic resistance can be used for selection (Fraley et al. (1983) *Proc. Natl. Acad. Sci. USA* 80:4803-4807). Unique restriction enzyme sites at the 5' and 3' ends of the cassette can allow for easy insertion into a pre-existing vector.

Other binary vector systems that can be used for *Agrobacterium*-mediated transformation are described in, for example, PCT Publication No. WO0020612. Further discussion of *Agrobacterium*-mediated transformation is found in Gelvin (2003) *Microbiol. Mol. Biol. Reviews* 67(1):16-37, and in Lorence and Verpoorte (2004) *Methods Mol. Biol.* 267:329-350.

In some embodiments, a system for rapid (e.g., transient) expression of proteins or polypeptides in plants can utilize an agrobacterial construct to deliver a viral expression system encoding the protein or polypeptide of interest. In particular, a "launch vector" can be prepared that contains agrobacterial sequences (including replication sequences) and plant viral sequences (including self-replication sequences) that carry a nucleic acid encoding the protein or polypeptide of interest. The launch vector can be introduced into plant tissue by, for example, agroinfiltration, which can allow for substantially systemic delivery. For transient transformation, non-integrated T-DNA copies of the launch vector can remain transiently present in the nucleus and can be transcribed, leading to expression of the encoded polypeptide (Kapila et al. (1997) *Plant Sci.* 122:101-108). Unlike expression from viral vectors, *Agrobacterium*-mediated transient expression does not lead to systemic expression of the gene of interest. An advantage of this system is the ability to clone genes larger than 2 kb to generate constructs that would be impossible to obtain with viral vectors (Voinnet et al. (2003) *Plant J.* 33:949-956). Furthermore, using such technique, it is possible to transform the plant with more than one transgene, such that multimeric proteins (e.g., antibodies or subunits of complexed proteins) can be expressed and assembled. Further, the possibility of co-expression of multiple transgenes by means of co-infiltration with different *Agrobacterium* can be achieved, either by separate infiltration or using mixed cultures.

In some embodiments, a launch vector can include sequences that allow for selection (or at least detection) in *Agrobacteria*, and also for selection/detection in infiltrated tissues. Furthermore, launch vectors typically include sequences that are transcribed in the plant to yield viral RNA production, followed by generation of viral proteins. Production of viral proteins and viral RNA can yield rapid production of multiple copies of RNA encoding the pharmaceutically active protein of interest. Such production can result in rapid protein production of the protein of interest in a relatively short period of time. Thus, a highly efficient system for protein production can be generated.

Agroinfiltration with viral expression vectors can be used to produce limited quantities of a particular polypeptide in order to verify the expression level before deciding whether it is worth generating transgenic plants. Alternatively or additionally, agroinfiltration techniques with viral expression vectors can be useful for rapid generation of plants capable of producing huge amounts of protein as a primary production platform. Thus, this transient expression system can be used on industrial scale.

Also provided herein are any of a variety of different Agrobacterial plasmids, binary plasmids, and derivatives thereof (e.g., pBI V, pBI 1221, and pGreen), which can be used in these and other aspects of the systems and methods described herein. Numerous suitable vectors are known in the art and can be directed and/or modified according to methods known in the art, or those described herein so as to utilize in the methods described provided herein.

An exemplary vector is pGRD4, which is based on Tobacco mosaic virus (TMV) and was engineered using the pGreen/pSoup system as a binary expression vector by introducing the Cauliflower mosaic virus 35 S promoter, the nos terminator, and the hammerhead ribozyme sequence from the launch vector pBID4. See, e.g., Shoji, et al. (2009) *Vaccine* 27: 1087-1092. Another exemplary launch vector is known as pBID4. This vector contains the 35S promoter of cauliflower mosaic virus (a DNA plant virus) that drives initial transcription of the recombinant viral genome following introduction into plants, and the nos terminator, the transcriptional terminator of *Agrobacterium* nopaline synthase. The vector further contains sequences of the tobacco mosaic virus genome including genes for virus replication (126/183K) and cell-to-cell movement (MP). The vector further contains a gene encoding a polypeptide of interest, inserted into a unique cloning site within the tobacco mosaic virus genome sequences and under transcriptional control of the coat protein subgenomic mRNA promoter. Because this "target gene" (i.e., gene encoding a protein or polypeptide of interest) replaces coding sequences for the TMV coat protein, the resultant viral vector is naked self-replicating RNA that cannot effectively spread and survive in the environment. Left and right border sequences (LB and RB) delimit the region of the launch vector that is transferred into plant cells following infiltration of plants with recombinant *Agrobacterium* carrying the vector. Upon introduction of *Agrobacteria* carrying this vector into plant tissue (typically by agroinfiltration but alternatively by injection or other means), multiple single-stranded DNA (ssDNA) copies of sequence between LB and RB are generated and released in a matter of minutes. These introduced sequences then can be amplified by viral replication. Translation of the target gene can result in accumulation of large amounts of the protein or polypeptide of interest in a short period of time.

In some embodiments, *Agrobacterium*-mediated transient expression can produce up to about 5 g or more of the target protein of interest per kg of plant tissue. For example, in some embodiments, up to about 4, 3, 2, 1, or 0.5 g of protein can be produced per kg of plant tissue. In some cases, at least about 20-500 mg, about 50-500 mg, about 50-200 mg, or about 50, 60, 70, 80, 90, 100, 110, 120, 130, 140, 150, 160, 170, 180, 190, or about 200, 250, 300, 350, 400, 450, 500, 550, 600, 650 700, 750, 800, 850, 900, 950, 1000, 1500, 1750, 2000, 2500, 3000 mg or more of target protein per kg of plant tissue can be produced. It is noted that, in some cases, the level of protein expression may be less, so that about 0.1 μg to 20 mg per kg of plant tissue (e.g., about 0.1-10 μg, about 10-50 μg, about 50-500 μg, or about 500 μg to 1 mg per kg of plant tissue) is produced, particularly in the case of the PNGase F polypeptide.

In some embodiments, these expression levels can be achieved within about 6, 5, 4, 3, or 2 weeks of infiltration. In some cases, such expression levels can be achieved within about 10, 7, 5, 4, 3, 2 days, or even 1 day, from introduction of the expression construct. Thus, the time from introduction (e.g., infiltration) to harvest typically is less than about 2 weeks, 10 days, 1 week or less. Further, a very attractive aspect of such embodiments is that protein can be produced within about 8 weeks or less from the selection of amino acid sequence (even including time for "preliminary" expression studies). Also, each batch of protein typically can be produced within about 8 weeks, 6 weeks, 5 weeks, or less. Those of ordinary skill in the art will appreciate that these numbers may vary somewhat depending on the type of plant used. Most sprouts, including peas, will fall within the numbers given. Other expected adjustments will be clear to those of ordinary skill in the art based on biology of the particular plants utilized.

Polynucleotide expression products can be isolated from the plant tissues that express them, and can be formulated for their intended use (e.g., as pharmaceutical or diagnostic agents, or as reagents). In some cases, an expression product can be formulated together with some or all of the plant tissues in which the product is expressed.

Where it is desirable to isolate an expression product from some or all of the plant tissue that expresses it, any available purification technique can be used. A wide range of fractionation and separation procedures are described in, for example, Scopes et al., *Protein Purification: Principles and Practice,* 3$^{rd}$ Ed.; Janson et al., *Protein Purification: Principles, High Resolution Methods, and Applications*, Wiley-VCH, 1998, Springer-Verlag, NY, 1993; and Roe, *Protein Purification Techniques*, Oxford University Press, 2001. Often, it can be useful to render the product more than about 50% pure (e.g., more than about 60%, 70%, 80%, 85%, 90%, 91%, 92%, 93%, 94%, 95%, 96%, 97%, 98%, or 99% pure).

Where it is desirable to formulate a product together with plant material, it often will be desirable to utilize a plant that is not toxic to the relevant recipient (e.g., a human or other animal). Relevant plant tissue (e.g., leaves) can be harvested and processed according to techniques known in the art, with due consideration to maintaining activity of the expressed product. In some embodiments, it can be useful to express the polynucleotide in an edible plant (and, specifically in edible portions of the plant) so that the material subsequently can be eaten. For instance, where the polynucleotide encodes a nutritionally relevant protein or a therapeutic protein that is active after oral delivery (when properly formulated), it can be useful to produce the protein in an edible plant portion, and to formulate the expressed polynucleotide for oral delivery together with some or all of the plant material with which the polynucleotide was expressed.

Where the polynucleotide encodes a vaccine component, the component can be formulated according to known techniques. For example, a vaccine component can be formulated together with one or more organic or inorganic, liquid or solid, pharmaceutically suitable carrier materials. A vaccine component produced as described herein can be employed in dosage forms such as tablets, capsules, troches, dispersions, suspensions, solutions, gelcaps, pills, caplets, creams, ointments, aerosols, powder packets, liquid solutions, solvents, diluents, surface active agents, isotonic agents, thickening or emulsifying agents, preservatives, and solid bindings, as long as the biological activity of the protein is not destroyed by such dosage form.

In general, such compositions can include any one or more of a variety of pharmaceutically acceptable carriers, adjuvants, or vehicles, or a combination thereof. Useful pharmaceutically acceptable carriers, adjuvants, and vehicles include, for example, solvents, dispersion media, coatings, antibacterial and antifungal agents, isotonic and absorption delaying agents, and the like, that are compatible with pharmaceutical administration. Exemplary materials are set forth below. It is noted that vaccine compositions can include one or more adjuvants to enhance the immunogenicity of the vaccine when administered to a subject. For example, a vaccine composition can include an adjuvant such as, without limitation, extracts of *Quillaja saponaria* (QS; including purified subfractions of food grade QS such as Quil A and QS-21), alum, aluminum hydroxide, aluminum phosphate, MF59, Malp2, incomplete Freund's adjuvant, complete Freund's adjuvant, and 3-O-deacylated monophosphoryl lipid A (3D-MPL). Further exemplary adjuvants include immunomodulatory oligonucleotides, such as unmethylated CpG sequences as disclosed in WO 96/02555. Combinations of different adjuvants, including those mentioned herein, also are contemplated. For example, QS21 can be formulated together with 3D-MPL, e.g., at a ratio of QS21:3 D-MPL on the order of 1:10 to 10:1; 1:5 to 5:1; or substantially 1:1. Doses of purified QS extracts suitable for use in a human vaccine formulation typically are from 0.01 mg to 10 mg per kilogram of body weight.

Where the polynucleotide encodes a therapeutic agent, the agent can be formulated according to known techniques. For example, an effective amount of a pharmaceutically active product can be formulated together with one or more organic or inorganic, liquid or solid, pharmaceutically suitable carrier materials. A pharmaceutically active product produced can be employed in dosage forms such as tablets, capsules, troches, dispersions, suspensions, solutions, capsules, creams, ointments, aerosols, powder packets, liquid solutions, solvents, diluents, surface active agents, isotonic agents, thickening or emulsifying agents, preservatives, and solid bindings, as long as the biological activity of the product is not destroyed by such dosage form.

Materials that can serve as pharmaceutically acceptable carriers include, without limitation, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants (e.g., sodium lauryl sulfate and magnesium stearate), coloring agents, releasing agents, coating agents, sweetening agents, flavoring agents, perfuming agents, preservatives, and antioxidants, according to the judgment of the formulator (see, also, *Remington's Pharmaceutical Sciences,* 15$^{th}$ Ed., E. W. Martin, Mack Publishing Co., Easton, Pa., 1975). For example, a polynucleotide expression product can be provided as a pharmaceutical composition by means of conventional mixing, granulating, dragee-making, dissolving, lyophilizing, or similar processes.

In some embodiments, the effect of a pharmaceutical preparation can be prolonged by slowing the absorption of the pharmaceutically active product (e.g., protein). For example, the absorption of a product that is subcutaneously or intramuscularly injected can be accomplished by using a liquid suspension of crystalline or amorphous material with poor water solubility. The rate of absorption of the product then depends upon its rate of dissolution, which in turn, may depend upon size and form. Alternatively, delayed absorption of a parenterally administered product can be accomplished by dissolving or suspending the product in an oil vehicle. Injectable depot forms are made by forming microencapsule matrices of the protein in biodegradable polymers such as polylactide-polyglycolide. Depending on the ratio of product to polymer and the nature of the particular polymer employed, the rate of release can be controlled. Examples of other biodegradable polymers include poly(orthoesters) and poly(anhydrides). Depot injectable formulations can be prepared by entrapping the product in liposomes or microemulsions, which are compatible with body tissues.

Enterally administered preparations of pharmaceutically active products can be introduced in solid, semi-solid, suspension or emulsion form, and can be compounded with any pharmaceutically acceptable carrier (e.g., water, suspending agents, and emulsifying agents). An expression product also can be administered by means of pumps or sustained-release forms, especially when administered as a preventive measure, so as to prevent the development of disease in a subject or to ameliorate or delay an already established disease.

Pharmaceutically active products, optionally together with plant tissue, can be particularly well suited for oral administration as pharmaceutical compositions. Harvested plant material can be processed in any of a variety of ways (e.g., air drying, freeze drying, or extraction), depending on the properties of the desired therapeutic product and its desired form. In some embodiments, such compositions can be ingested orally alone or ingested together with food or feed or a beverage. Compositions for oral administration can include transfected plants; extractions of transfected plants, and proteins purified from transfected plants provided as dry powders, foodstuffs, aqueous or non-aqueous solvents, suspensions, or emulsions. Examples of non-aqueous solvents include, without limitation, propylene glycol, polyethylene glycol, vegetable oil, fish oil, and injectable organic esters. Aqueous carriers include water, water-alcohol solutions, emulsions or suspensions, including saline and buffered medial parenteral vehicles including sodium chloride solution, Ringer's dextrose solution, dextrose plus sodium chloride solution, Ringer's solution containing lactose, and fixed oils. Examples of dry powders include any transfected plant biomass that has been dried (e.g., freeze dried, air dried, or spray dried). For example, a plant can be air dried by placing it in a commercial air dryer at about 120 degrees Fahrenheit until the biomass contains less than about 5% moisture by weight. The dried plant can be stored for further processing as a bulk solid, or can be further processed by grinding to a desired mesh sized powder. Alternatively, freeze-drying may be used for products that are sensitive to air-drying. Products can be freeze dried by placing them into a vacuum drier and drying frozen under a vacuum until the biomass contains less than about 5% moisture by weight. The dried material can be further processed as described herein.

Another method that can be used to obtain pharmaceutically active products expressed in plants is by extraction. Transfected plants can be extracted to remove the desired products from residual biomass, thereby increasing the concentration and purity of the product. Plants also can be extracted in a buffered solution.

For example, fresh harvested plants can be transferred at a ratio of one to one by weight into an amount of ice-cold water that has been buffered with, e.g., phosphate buffer. Protease inhibitors also can be added. The plants can be disrupted by vigorous blending or grinding while suspended in the buffer solution, and the extracted biomass can be removed by filtration or centrifugation. The polypeptide product carried in solution can be further purified by additional steps, or can be converted to a dry powder by freeze-drying or precipitation. Extraction also can be carried out by pressing in a press or by being crushed as they are passed through closely spaced rollers. Fluids expressed from crushed plants can be collected and processed according to methods known in the art. Extraction by pressing allows the release of the products in a more concentrated form, but the overall yield of the product may be lower than if the product was extracted in solution.

Protein preparations (e.g., extractions, powders, dried preparations, and purified protein products) also can be in encapsulated form with or without one or more excipients as noted above. Solid dosage forms of tablets, dragees, capsules, pills, and granules can be prepared with coatings and shells such as enteric coatings, release controlling coatings and other coatings well known in the pharmaceutical formulating art. The active product in such solid dosage forms can be admixed with at least one inert diluent such as sucrose, lactose or starch. Such dosage forms also can include additional substances other than inert diluents, e.g., tableting lubricants and other tableting aids such a magnesium stearate and microcrystalline cellulose. In the case of capsules, tablets and pills, the dosage forms may also comprise buffering agents and/or opacifying agents, and can be of a composition such that they release the active ingredient(s) only, or preferentially, in a certain part of the intestinal tract, for example. Examples of embedding compositions that can be used include polymeric substances and waxes.

Pharmaceutical compositions can be administered therapeutically or prophylactically. In some embodiments, a composition can be used to treat or prevent a disease. For example, any individual who suffers from a disease or who is at risk of developing a disease may be treated. It will be appreciated that an individual can be considered at risk for developing a disease without having been diagnosed with any symptoms of the disease. For example, if the individual has a particular genetic marker identified as being associated with increased risk for developing a particular disease, that individual will be considered at risk for developing the disease. Similarly, if members of an individual's family have been diagnosed with a particular disease, e.g., cancer, the individual may be considered to be at risk for developing that disease.

Liquid dosage forms for oral administration include, but are not limited to, pharmaceutically acceptable emulsions, microemulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Compositions for rectal or vaginal administration can be suppositories, which can be prepared by mixing a composition with one or more suitable non-irritating excipients or carriers such as cocoa butter, polyethylene glycol or a suppository wax which are solid at ambient temperature but liquid at body temperature and therefore melt in the rectum or vaginal cavity and release the active protein.

Dosage forms for topical or transdermal administration of a pharmaceutical composition include ointments, pastes, creams, lotions, gels, powders, solutions, sprays, inhalants or patches. The active product, or preparation thereof, is admixed under sterile conditions with a pharmaceutically acceptable carrier and any needed preservatives or buffers as may be required. Ophthalmic formulation, eardrops, and eye drops are also contemplated as being within the scope of this document. Additionally, this document contemplates the use of transdermal patches, which can provide controlled delivery of a pharmaceutically active protein to the body. Such dosage forms can be made by suspending or dispensing the pharmaceutically active product in the proper medium. Absorption enhancers can also be used to increase the flux of the pharmaceutically active protein across the skin. The rate can be controlled by either providing a rate controlling membrane or by dispersing the pharmaceutically active protein in a polymer matrix or gel.

Compositions typically are administered in such amounts and for such time as is necessary to achieve the desired result. In some embodiments, a "therapeutically effective amount" of a pharmaceutical composition is an amount effective for treating, attenuating, or preventing a disease in a host. Thus, the "amount effective to treat, attenuate, or prevent disease," as used herein, refers to a nontoxic but sufficient amount of the pharmaceutical composition to treat, attenuate, or prevent disease in any host.

The exact amount required will vary from subject to subject, depending on the species, age, and general condition of the subject, the stage of the disease, the particular pharmaceutical mixture, its mode of administration, and the like. Infected plants and/or protein preparations thereof are preferably formulated in dosage unit form for ease of administration and uniformity of dosage. The expression "dosage unit form," as used herein, refers to a physically discrete unit of pharmaceutically active polynucleotide expression product appropriate for the patient to be treated. It will be understood, however, that the total daily usage of a composition is preferably decided by an attending physician within the scope of sound medical judgment. The specific therapeutically effective dose level for any particular patient or organism may depend upon a variety of factors including the disorder being treated and the severity of the disorder; the activity of the specific compound employed; the specific composition employed; the age, body weight, general health, sex of the patient, diet of the patient, pharmacokinetic condition of the patient, the time of administration, route of administration, and rate of excretion of the specific compound employed; the duration of the treatment; drugs used in combination or coincidental with the specific compound employed; and like factors well known in the medical arts.

The invention will be further described in the following examples, which do not limit the scope of the invention described in the claims.

EXAMPLES

Example 1

Materials and Methods

Cloning and expression of PNGase F in *N. benthamiana*: The PNGase F gene was optimized for expression in *N. benthamiana* (for codon optimization, mRNA stability, RNA destabilizing sequence knockout, etc.) and synthesized by GENEART AG (Regensburg, Germany) with flanking PacI (5'-terminus) and XhoI (3'-terminus, after stop codon) sites. To express PNGase F in *N. benthamiana* plants using a transient expression system, nucleotides encoding the signal peptide (amino acids 1-40) were removed from the PNGase F sequence, and nucleotides encoding the tobacco PR-1a signal peptide (MGFVLFSQLPSFLLVSTLLLFLV-ISHSCRA; SEQ ID NO:3) were added to the 5' end of the coding sequence. Sequences encoding an ER retention signal (KDEL; SEQ ID NO:5) and a FLAG epitope affinity purification tag (SEQ ID NO:4) were added to the 3' end. The resulting sequence was inserted into the launch vector pGRD4 (Roy et al. (2010) *Virol.* 405(1):93-99) or the binary expression vector pBI121 (Chen et al. (2003) *Mol. Breeding* 11:287-293) using the PacI-XhoI restriction enzyme sites to obtain pGRD4- and pBI-PNGase F, respectively. pGRD4- and pBI-PNGase F (together with pSoup for pGRD4-PNGase F, which provides replication functions in trans (Hellens et al. (2000) *Plant Mol. Biol.* 42(6):819-832), were then introduced into *Agrobacterium tumefaciens* strain GV3101. The resulting bacterial strain was grown in BBL medium (10 g/L soy hydrolysate, 5 g/L yeast extract, 5 g/L NaCl, and 50 mg/L kanamycin) overnight at 28° C. Bacteria were introduced by manual infiltration into 6-week-old *N. benthamiana* plants grown in soil. Five, six and seven days after infiltration, leaf tissue was harvested and homogenized using a bullet blender. Extracts were clarified by centrifugation (13,000×g) and used for further analyses.

Purification of PNGase F: PNGase F was purified using anti-FLAG antibody-column chromatography to confirm its in vitro de-glycosylation activity. Eight grams of frozen leaves were ground in 24 ml of TBS buffer (50 mM Tris-HCl, pH 7.4, 150 mM NaCl) using a mortar and pestle. Plant debris was removed by filtration through Miracloth (Calbiochem, San Diego, Calif.) followed by centrifugation at 13,000×g for 10 minutes, and then filtration through a 0.22 micron syringe filter (ACROS organics). A column containing 1 ml of Anti-FLAG M2 affinity gel (Cat. no. A2220, Sigma, St. Louis, Mo.) was prepared according to the manufacturer's instructions, and 24 ml of clear supernatant was mixed with 1 ml of the gel and rotated at 4° C. for 1 hour, after which the whole mixture was returned to the column and the column was washed with 20 volumes of TBS buffer. Bound proteins were eluted using 0.1 M glycine buffer, pH 3.5 in 6 tubes of 500 µl volume, and 5 µl of 1 M Tris-Cl was immediately added to each tube to neutralize the glycine buffer.

De-glycosylation ability of PNGase F purified from *N. benthamiana*: To test the de-glycosylation ability of purified PNGase F in vitro and also to compare the extent of de-glycosylation of 48F1 in vitro and in vivo, different amounts (10-200 ng) of purified PNGase F were incubated with Pfs48F1 (expressed in and purified from *N. benthamiana*) at 37° C. for 1 hour in PBS buffer, and 0.75 µg non-deglycosylated and de-glycosylated Pfs48F1 along with in vivo de-glycosylated PFs48F1 were analyzed by Western blotting. To test whether expressed PNGase F de-glycosylated *N. benthamiana* proteins, total proteins from control (non-transformed) *N. benthamiana* and from *N. benthamiana* transformed with bacterial PNGase F, PNGase F+p19 (plant suppressor of RNA silencing) and p19, were compared by SDS-PAGE. Leaf punches (20 mg each) from each leaf were ground using a bullet blender (Zymo research) at 4° C. for 2 minutes, and after two centrifugation steps at 13,000×g for 10 minutes, samples were boiled with 1× SDS-sample buffer and 10 µl of each sample was loaded into SDS-PAGE.

Co-expression of Pfs48F1, *B. anthracis* PA, and antibody against *B. anthracis* PA (C) with PNGase F: To co-express Pfs48F1, *B. anthracis* PA, and antibody against *Bacillus anthracis* PA with PNGase F, the pBI-Pfs48F1/pGRD4-PNGase F, pGRD4-PA83-1/pBi-PNGase F and pBI-PA/pGRD4-PNGase F constructs were used for infiltration into *N. benthamiana* plants. The sequences of Pfs48F1 (amino acids 28-401, GENBANK® accession no. EU366251), *B. anthracis* PA (amino acids 30-764, GENBANK® accession no. AAA22637), and HC and LC of PA antibody (Mett et al. (2011) *Hum. Vaccin.* 7:183-190) were inserted into the launch vector (pGRD4) or binary expression vector pBI vector using the PacI and XhoI restriction enzyme sites. *Agrobacterium* transformation, plant infiltration, and leaf protein extraction were performed as described above.

Western blot analysis: Protein samples from infiltrated *N. benthamiana* were prepared as follows. Leaf samples were taken at 5, 6, and 7 DPI, and were ground in extraction buffer for TSP, extraction buffer with 0.5% Triton X-100 for TSPT, and extraction buffer with 1× sodium dodecyl sulfate (SDS) sample buffer for TP. These proteins samples were centrifuged at 13,000×g for 10 minutes to remove insoluble debris, and were separated on 10% SDS-polyacrylamide gels, transferred onto a polyvinylidene fluoride membrane (Millipore; Billerica, Mass.) and blocked with 0.5% I-block (Applied Biosystems; Carlsbad, Calif.). For detection of Pfs48F1, the membrane was incubated with a primary antibody against poly-His (Roche Applied Science; Indianapolis, Ind.), followed by horseradish peroxidase (HRP)-conjugated goat anti-mouse antibody. For detection of PNGase F, anti-FLAG monoclonal antibody (Cat. No. F2555; Sigma) produced in rabbit was used as the primary antibody, and horseradish peroxidase (HRP)-conjugated anti-rabbit IgG was used as the secondary antibody. Proteins reacting with the anti-His/FLAG antibodies were visualized using SUPERSIGNAL® West Pico Chemiluminescent Substrate (Pierce Biotechnology; Rockford, Ill.). The image was taken using GeneSnap software on a GENEGNOME™ and quantified using Gene Tools software (Syngene; Frederick, Md.).

Plasmid construction for chloroplast-targeted expression of Pfs48F1: A gene encoding a 38-amino-acid sequence (MLIAHPQAFPGAIAAPISYAYAVKGRKPRFQT AKGSVRI; SEQ ID NO:6) encompassing the arm domain of the Cucumber Necrosis Virus Coat Protein, which has been shown functions as a chloroplast transit peptide (Xiang et al., (2006) *J. Virol.* 80 (16):7952-64) in infected plants (*N. benthamiana*) was codon-optimized for *N. benthamiana* and assembled from two oligos:

1) 5'-AGTCTTAATTAAATGCTTATTGCTCACC-CACAAGCTTTCCCAGGAG CTATTGCTGCTC-CAATTTCTTACGCTTACGCTG-3' (SEQ ID NO:7); and 2) 5'-GAGTCCGTCTCAAATCCTCACAGATCCCT-TAGCAGTCTGGAACCTT GGCTTCCTACCCTT-CACAGCGTAAGCGTAAGAAA-3' (SEQ ID NO:8).

PCR amplification was performed using 5'-AGTC ttaattaaATGCTTATTGCTC ACCCAC-3' (forward) (SEQ ID NO:9) and 5'-gagtccgtctcaAATCCTCACAGAT-3' (reverse) (SEQ ID NO:10) primers. PacI and BsmBI restriction sites are underlined. PCR amplification was performed using Phusion Flash High Fidelity PCR Master Mix (New England Biolabs) with 35 cycles of denaturation at 98° C. for 1 second, annealing at 58° C. for 5 seconds, and extension at 72° C. for 7 seconds, with a final extension at 72° C. for 60 seconds, using the oligos described above as the DNA template. PCR product was digested with PacI and BsmBI for further cloning. Amplification of Pfs48F1 gene was performed using 5'-gagtccgtctcaGATTAACAACGAT-TTCTGCAAGC-3' (forward) (SEQ ID NO:11) and 5'-gagtc ctcgagTCAGTGGTGGTGATGGTGATGA-3' (reverse) (SEQ ID NO:12) primers and pGRD4-48F1 as DNA template. BsmBI and XhoI restriction sites are underlined. PCR was performed using Phusion Flash High Fidelity PCR Master Mix (New England Biolabs, cat no. F-548L) with 35 cycles of denaturation at 98° C. for 10 seconds, annealing at 65° C. for 5 seconds, and extension at 72° C. for 15 seconds, with a final extension at 72° C. for 60 seconds. PCR product was digested with BsmBI and XhoI. PCR products were cloned into pGDR4 vector digested with PacI and XhoI to generate the Arm-Pfs48f1 expression plasmid. The protein was introduced and expressed in *N. benthamiana* plants as described above.

Purification of in vivo deglycosylated Pfs48F1: For purification of the deglycosylated Pfs48F1 recombinant protein from *N. benthamiana* plants, 50 g of plant material, infiltrated with pBI-Pfs48F1 and pGRD4-PNGase F, was homogenized in 150 ml extraction buffer and incubated with 0.5% Triton (final concentration) for 20 minutes at 4° C. with stirring. After incubation, the lysate was centrifuged at 48,000 g for 40 minutes, and crude extract was filtered through Miracloth, loaded onto 5 mL His Trap FF (Cat. No. 17-5255-01, GE Healthcare), and washed with 15 volumes of 50 mM sodium phosphate buffer, pH 8.0, 0.5 M NaCl, and 20 mM imidazole. Proteins were eluted with 50 mM sodium phosphate buffer, pH 8.0, 0.5 M NaCl, and 100 mM imidazole. Eluted fraction was concentrated and dialyzed against PBS, pH 7.5.

Purification of Pfs48F1 from *N. benthamiana* plants: For purification of Pfs48F1 recombinant protein from *N. benthamiana* plants, 750 g of plant material was homogenized in 2.25 L extraction buffer and incubated with 0.5% Triton (final concentration) for 20 minutes at 4° C. with stirring. After incubation, the lysate was centrifuged at 48,000 g for 40 minutes, and crude extract was filtered through Miracloth and loaded onto a column with 70 mL Chelating Sepharose Big Beads charged with Ni. The column was washed with 15 volumes of 50 mM sodium phosphate buffer, pH 8.0, 0.5 M NaCl, 20 mM imidazole, and 20% glycerol. Proteins were eluted with 50 mM sodium phosphate buffer, pH 8.0, 0.5 M NaCl, 300 mM imidazole, and 20% glycerol. The eluted protein fraction was dialyzed first against 10 mM sodium phosphate buffer, pH 6.5, 50 mM NaCl, 10 mM EDTA, and 10% glycerol, and then into 10 mM sodium phosphate buffer, pH 6.5, 10% glycerol. After spin down, the dialyzed sample was loaded into 5 mL Capto Q, equilibrated with 10 mM sodium phosphate buffer, pH 6.5, and 10% glycerol. Proteins were eluted with 10 mM sodium phosphate buffer, pH 6.5, 10% glycerol, and 600 mM NaCl. The eluted fraction was concentrated up to 2.6 mg/mL and dialyzed against PBS, pH 7.5.

Comparative ELISA analysis: Recognition of the deglycosylated and glycosylated forms of Pfs48F1 by rat mAbs raised against various epitopes (I, IIb, III and V) of the *Plasmodium falciparum* surface protein Pfs48/45 (Outchkourov et al. (2007) *J. Biol. Chem.* 282:17148-17156; and Roeffen et al. (2001) *Exp. Parasitol.* 97:45-49) was assessed using ELISA. ELISA plates (96-well MaxiSorp plates [NUNC, Rochester, N.Y.]) were coated with an anti-4×His mAb (Qiagen Cat. No. 34670; Valencia, Calif.) in PBS at 50 μL/well (5 μg/mL) overnight at 4° C. After blocking with 0.5% I-block in PBS, desired amounts (1-1000 ng) of the deglycosylated and glycosylated forms of Pfs48F1 were added and incubated for 2 hours. After washing the plates, 50 μL (2 μg/mL in I-block) of various mAbs raised against Pfs48/45 were added and incubated for 2 hours. Bound antibodies were detected using a HRP-conjugated goat anti-rat polyclonal antibody (1:25,000 in I-block) and visualized using o-phenylenediamine (OPD) as a substrate, at a wavelength of 490 nm.

Affinity analysis of mAb V binding to glycosylated and deglycosylated Pfs48F1 variants: The $K_d$ of mAb V binding to glycosylated and deglycosylated (in vitro and in vivo) variants of Pfs48F1 were assessed using the KinExA 3200 instrument (Sapidyne, Boise, Id.; Blake et al. (1999) *Anal. Biochem.* 272:123-134) by determining the amount of free antibody remaining in solution after equilibration with the respective Pfs48F1 binding partner was reached. mAb V concentrations were held constant while the selected glycosylated or deglycosylated Pfs48F1 protein was serially diluted. mAb V was mixed with glycosylated Pfs48F1 at 107 nM, 69 nM and 22 nM; with in vitro deglycosylated Pfs48F1 at 42.4 nM, 16.2 nM and 4 nM; and with in vivo deglycosylated Pfs48F1 at 42.4 nM, 10.6 nM and 4 nM. Running buffer was 1× PBS, pH 7.5 with 0.02% sodium azide as a preservative. The samples and the secondary antibody were diluted using running buffer augmented with 1 mg/mL bovine serum albumin (BSA). The secondary antibody was Dylight 649-conjugated goat anti-rat (Jackson ImmunoResearch, West Grove, PA) used at 0.5 μg/mL. PNGase-treated Pfs48F1 was used as the coating reagent for the flow cell bead pack (PMMA beads, Sapidyne) in all experiments. The flow rate for all samples and for the labeling antibody was 0.25 mL/min. Sample volume ranged from 0.35-3.0 mL.

Titration data resulting from three different antibody concentrations equilibrated with each Pfs48F1 were fit to a global 1:1 binding model included in the KinExA software (version 3.1.2). Data generated for mAb V and Pfs48F1 were fit to the standard 1:1 binding model where $K_d$, active binding site concentration (ABC), and signal maximums and minimums were determined. In this case, the concentration of Pfs48F1 (glycosylated) was determined by densitometry versus BSA using Coomassie-stained SDS-PAGE. Data generated for mAb V with the deglycosylated versions of Pfs48F1 were fit to the same 1:1 binding model, but using an unknown antigen concentration model (Xie et al. (2005) *J. Immunol. Meth.* 304:1-14). In this model, the $K_d$ and signal parameters were determined from the fit as well as the LCM. The LCM relates an unknown concentration of the ligand to the determined ABC (from the experiment with mAb V and Pfs48F1), which allows direct comparison of binding data when the concentration of antigen is less well characterized or unknown. In this case, the concentration of the in vivo deglycosylated Pfs48F1 was estimated using Western blotting, so the binding analysis was standardized to the concentration of glycosylated Pfs48F1.

Qualitative analysis of mAb III inhibition by glycosylated and deglycosylated Pfs48F1 variants: Qualitative analysis of mAb III inhibition by the Pfs48F1 variants (glycosylated and PNGase F-deglycosylated in vitro and in vivo) was performed using a KinExA 3200 instrument. Solutions containing mAb III at 140 nM binding site and 70 nM nominal protein concentrations and one of the Pfs48 variants (glycosylated or PNGase F-deglycosylated) at a final concentration of 250 nM were prepared and incubated, and the amount of free mAb III in each reaction mixture was determined using the KinExA instrument. The initial concentration of each Pfs48F1 variant in the reaction mixture was based on the LCM value determined in the mAb V experiments. The signal generated by mAb III in the solution without Pfs48F1 was considered as 100%.

Example 2

Expression of Bacterial PNGase F in *N. benthamiana*

The PNGase F coding sequence (314 amino acids representing the full length, catalytically active protein without the signal sequence) was optimized (FIG. 1), cloned into the pGRD4 expression vector, and expressed in *N. benthamiana* as described in Example 1. The average expression level of PNGase F was approximately 150 mg/kg of fresh biomass. Expression of PNGase F was confirmed by immuno-blot analysis using anti-FLAG monoclonal antibody (see FIG. 2A).

Example 3

Co-Expression of Pfs48F1 with Bacterial PNGase F

Pfs48F1E malaria vaccine candidate was transiently co-expressed with bacterial PNGase F in *N. benthamiana* to test whether N-linked oligosaccharides would be cleaved from Pfs48F1 in an in vivo environment. PNGase F was expressed with a FLAG epitope followed by a C-terminal ER retention signal, KDEL (SEQ ID NO:5). The results are presented in FIG. 2. Co-expressed PNGase F was active in vivo and successfully cleaved the N-linked oligosaccharides from Pfs48F1. Pfs48F1 produced after PNGase F digestion migrated similarly to Pfs48F1 that was enzymatically de-glycosylated using a commercial source of PNGase F (New England Biolabs) in vitro (FIG. 2B). The expression level of de-glycosylated Pfs48F1 was about 50 mg/kg when Pfs48F1 (pGRD4-PNGase F) was co-expressed with PNGase F (pBI121-Pfs48F1). Solubility of de-glycosylated Pfs48F1 was about 95 percent. Expression of PNGase F was confirmed by immuno-blot analysis (FIG. 2A).

Example 4

Figure 4A:
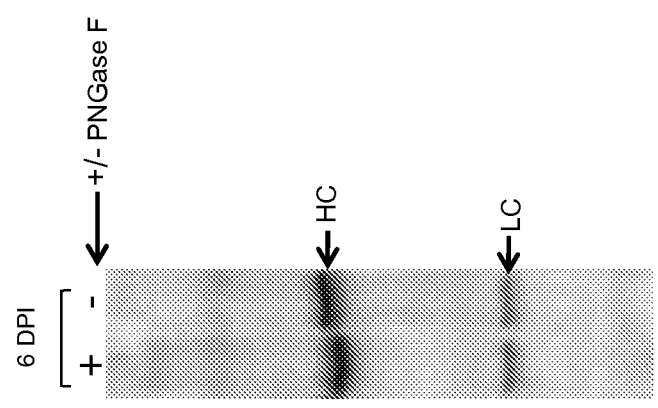
FIG. 4 depicts Western blots showing co-expression of protective antigen (PA) of *Bacillus anthracis* (FIG. 4A) and antibody against *B. anthracis* PA (FIG. 4B) with PNGase F. For co-expression of PNGase F with *B. anthracis* PA and antibody against *B. anthracis* PA, pGRD4-PA83-1/pBi-PNGase F and pBI-PA-A/pGRD4-PNGase F constructs were used for infiltration into *N. benthamiana* plants. Leaf samples (taken at 5 DPI from plants infiltrated with PA and at 6 DPI from plants infiltrated with antibody against antibody against *B. anthracis* PA) were ground in extraction buffer, centrifuged, and diluted in SDS-sample buffer. 10 µl samples were run on SDS-PAGE prior to Western blot analysis. PA bands were probed with the anti-His monoclonal antibody. Antibodies against *B. anthracis* PA were probed with rabbit anti-alpha human antibodies.
Figure 4B:
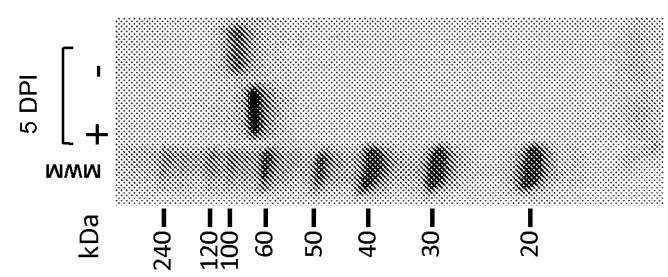

Co-Expression of Protective Antigen (PA) of *Bacillus anthracis* and Antibody Against PA of *Bacillus anthracis* (C) with PNGase F The in vivo de-glycosylation strategy was applied to two other glycoproteins—protective antigen (PA) of *B. anthracis*, and antibody against *B. anthracis* PA. Co-expression results are presented in FIG. 4. A mobility shift was observed in the heavy chain (HC), which has one glycosylation site, but there was no shift in the light chain (LC) that lacks glycosylation sites. These results, along with co-expression with Pfs48F1, indicated that PNGase F successfully cleaved the N-linked glycans from all tested glycoproteins, and that this strategy can be used to produce therapeutic proteins and antibodies in a de-glycosylated form in *N. benthamiana* using a transient expression system.

Example 5

Purification of PNGase F from *N. benthamiana*

Figure 3B:
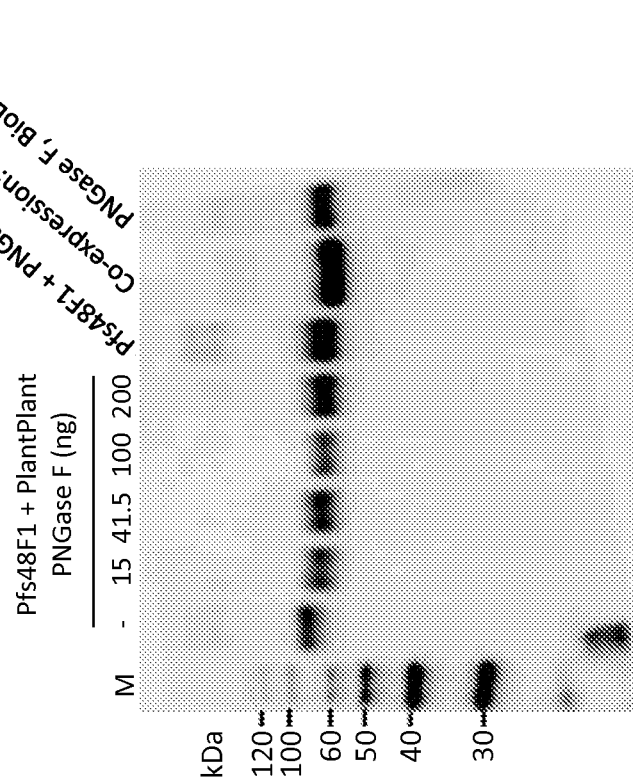
FIG. 3 shows an SDS-polyacrylamide gel electrophoresis (PAGE) gel of purified PNGase F (FIG. 3A) and a Western blot comparing de-glycosylation of Pfs48F1 under in vitro and in vivo conditions (FIG. 3B). For FIG. 3A, PNGase F was purified from *N. benthamiana* using an anti-FLAG agarose column as described in Example 1 below, and purified protein was analyzed by SDS-PAGE. For the Western blot shown in FIG. 3B, purified Pfs48F1E was incubated under non-denaturing conditions with increasing amounts of PNGase F purified from plants, or with PNGase F obtained from New England Biolabs. Pfs48F1 protein was detected with the anti-His tag monoclonal antibody. De-glycosylation of Pfs48F1 by purified or commercial PNGase F was compared with de-glycosylation of Pfs48F1 in vivo by co-expressed PNGase F (second lane from right). "MWM" refers to molecular weight markers [SEEBLUE® Plus2 Pre-Stained Standard (FIG. 3A), and MAGICMARK™ XP Western Protein Standard (FIG. 3B); both markers from Invitrogen; Carlsbad, Calif.].
Figure 3A:
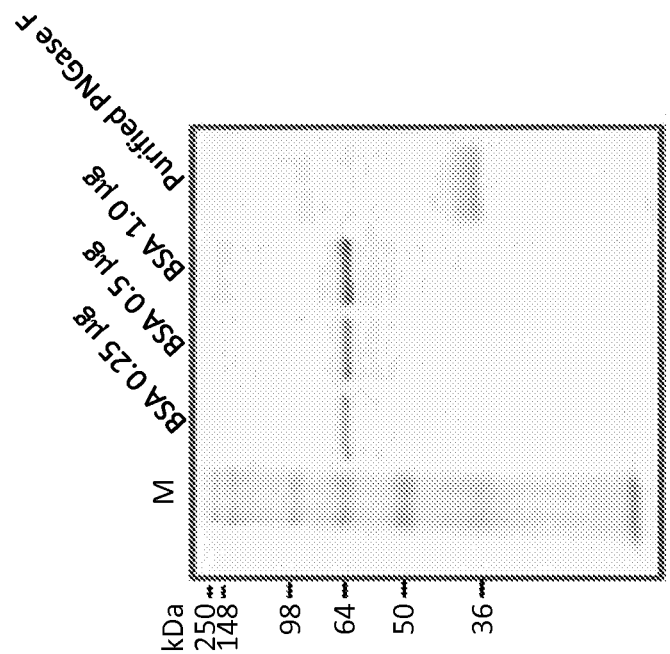

To confirm in vitro activity of PNGase F, the recombinant enzyme was purified from *N. benthamiana* using an anti-FLAG agarose column as described in Example 1. The purified PNGase F protein was analyzed by SDS-PAGE (FIG. 3A). Coomassie staining showed that purified PNGase F had a high level of homogeneity. The de-glycosylation ability of purified PNGase F was tested using Pfs48F1E glycoprotein, expressed in *N. benthamiana*. The results are presented in FIG. 3B. Purified plant PNGase F was able to de-glycosylate Pfs48F1 in vitro, and the degree of de-glycosylation was increased by increasing the amount of purified PNGase F. De-glycosylation of Pfs48F1 by purified plant-produced PNGase F and by commercial PNGase F (New England Biolabs; Ipswich, Mass.) was compared with the de-glycosylation of Pfs48F1 in vivo by co-expressed PNGase F.

Example 6

Evaluation of Antigenicity of De-Glycosylated and Glycosylated Forms of Pfs48F1

In order to evaluate antigenicity (ability to bind antibody) of de-glycosylated and glycosylated forms of Pfs48F1, the two forms of proteins are tested using ELISA as mentioned in Example 1. Four mAbs that detect epitopes I, IIb, II and V of *P. falciparum* surface protein were used in the test. Results are shown in FIGS. 5A, 5B, 5C, and 5D, respectively. Compared to the glycosylated form (diamonds), the de-glycosylated Pfs48F1 (squares) were more readily recognized by three out of four mAbs. The mAb recognizing IIb (mAb IIb; FIG. 5B) showed only background-level signal with the glycosylated form of Pfs48F1, and the de-glycosylated counterpart did not show better affinity. This suggests that the poor recognition of the epitope by mAb IIb is due to reasons other than aberrant glycosylation of the Pfs48F1 protein.

Example 7

Affinity of mAb V Binding to Plant-Produced Pfs48F1

The mAb raised against epitope V of Pfs48F1 was selected to quantitatively evaluate the affinity of the antibody to glycosylated and de-glycosylated Pfs48F1 proteins. Evaluations were conducted as described in Example 1. FIG. 6A illustrates results obtained with glycosylated Pfs48F1, where the $K_d$ value was found to be 11.48 nM. A stronger affinity was observed from in-vitro de-glycosylated Pfs48F1, which showed a $K_d$ value of 4.76 nM (FIG. 6B). In-vivo de-glycosylated Pfs48F1 showed the strongest affinity to mAB V, with a $K_d$ value of 2.57 nM. As noted in FIG. 3B, in vivo de-glycosylation ($2^{nd}$ lane from right) was more effective in removing carbohydrates than in-vitro treatments ($2^{nd}$-$6^{th}$ lanes from left). The results shown in FIG. 6, combined with the results shown in FIG. 3B, showed that extensive de-glycosylation of Pfs48F1 in vivo further improves the affinity of the protein to mAb V.

Example 8

Qualitative Inhibition Comparison Between mAb III and Pfs48F1 Variants

Figure 7:
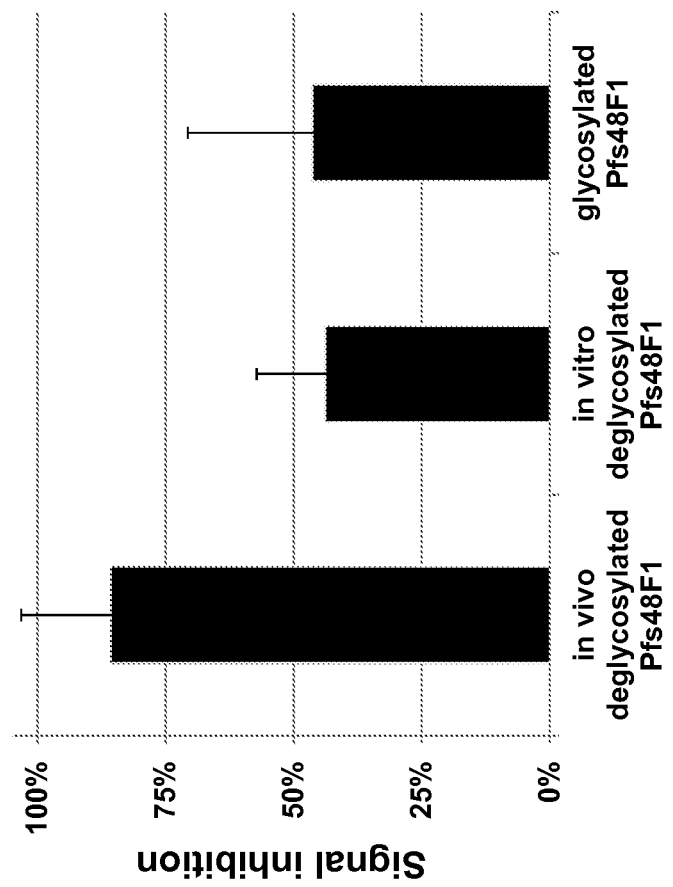
FIG. 7 illustrates affinity of mAb binding to Pfs48F1 variants, as shown by inhibition of signal generated from free mAb III by binding of the Pfs48F1 variants.

The effect of glycosylation on the affinity of Pfs48F1 to mAb III was examined as described in Example 1. With the signal level from unbound mAb set as 100%, the binding of a ligand to the mAb will lead to "inhibition" of the signal. The extent of signal inhibition can thus be interpreted as a measure of binding affinity. When added to the solution of mAb III, all three Pfs48F1 variants led to signal inhibition as shown in FIG. 7. The strongest inhibition of signal was observed when the mAb was mixed with in-vivo de-glycosylated Pfs48F1. These results showed that in vivo de-glycosylation led to stronger affinity and improved antigenicity of Pfs48F1 in comparison to in vitro de-glycosylated Pfs48F1 and glycosylated Pfs48F1.

Example 9

Comparison with Pfs48F1 Targeted to Chloroplasts

Plant chloroplasts can be used for production of proteins. (Verma et al., (2008) *Nature Protocols* 3:739-758). The use of plant chloroplasts, termed Chloroplast Transformation Technology (CTT) can produce properly folded and correctly disulfide-bonded proteins in large quantities. Like bacterial expression systems, chloroplasts do not glycosylate their proteins.

In order to compare products obtained by in vivo de-glycosylation and CTT, Pfs48F1 was expressed in plant cells using a conventional method that bypasses glycosylation by targeting the protein to the chloroplast. A Pfs48F1 fusion to a 38 amino acid chloroplast-targeting signal (Arm-Pfs48F1)

was expressed in cytoplasm as explained in Example 1, and its antigenicity was compared with in vivo de-glycosylated Pfs48F1.

Figure 8:
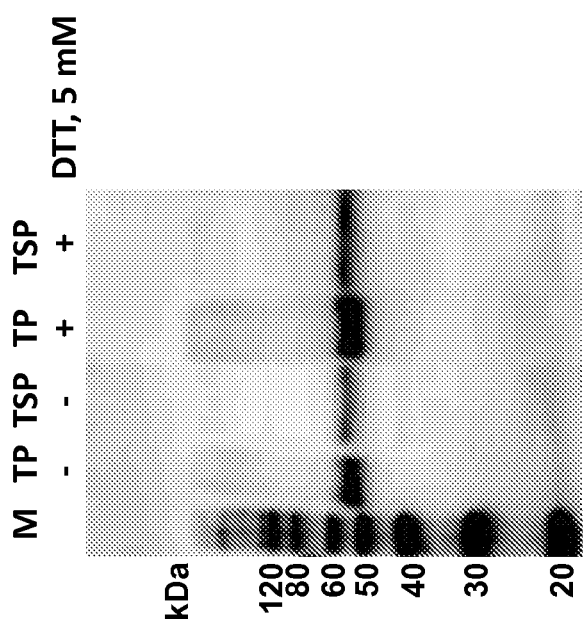
FIG. 8 depicts a western blot of Arm-Pfs48F1 expressed in transformed *N. benthamiana*. Leaf samples of transformed plants were taken at 7 DPI, and were ground in extraction buffer for TSP or extraction buffer with SDS for TP, with or without dithiothreitol (DTT), as indicated.
Figure 9B:
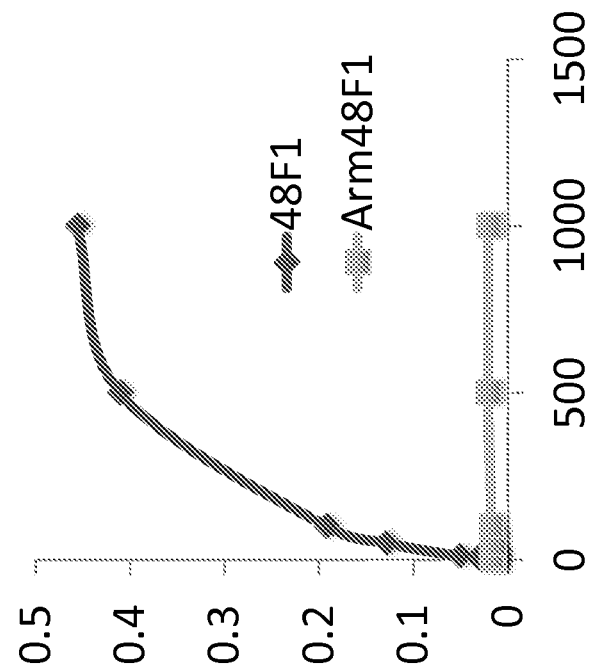
FIG. 9 illustrates binding affinity of in vivo de-glycosylated Pfs48F1 and chloroplast-targeted Arm-Psf48F1 to mAb III (FIG. 9A) and mAb V (FIG. 9B) as determined from a comparative ELISA analysis.
Figure 9A:
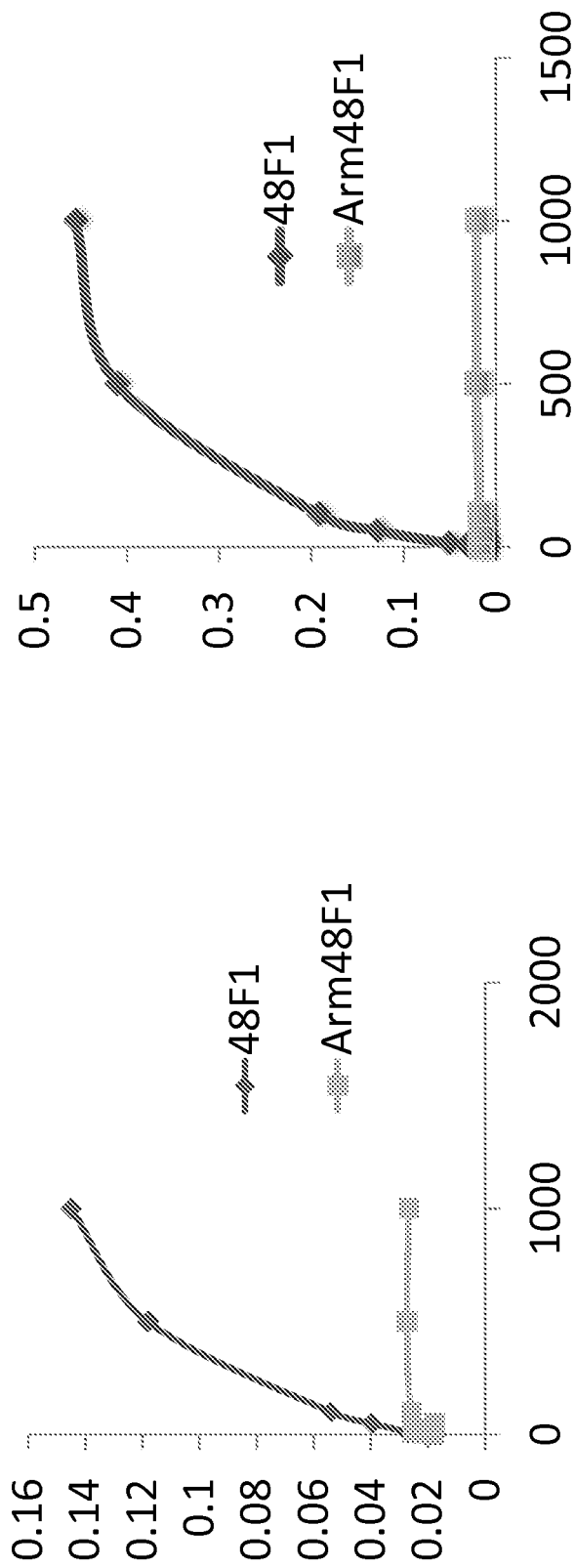

A western blot of leaf samples from *N. benthamiana* transformed to express Arm-Pfs48F1 showed that the Arm-Pfs48F1 protein was successfully expressed in the targeted plants, and that a significant portion of the total expressed Pfs48F1 was found in the soluble fraction as detected from the TSP lanes (FIG. 8). A comparative ELISA analysis was performed using in vivo de-glycosylated Pfs48F1 and Arm-Pfs48F1 as explained in Example 1. FIG. 9 shows results obtained with mAb III (panel A), and with mAb V (panel B). Although the method of chloroplast targeting prevents Arm-Pfs48F1 from being glycosylated, the resulting protein did not show a detectable level of affinity for the antibodies. On the other hand, in vivo de-glycosylated Pfs48F1 showed affinity for both antibodies, as evident from the increase in signal as more protein was added to the reaction. These results showed that in vivo de-glycosylation of Pfs48F1 by PNGase-F resulted in a protein that was more readily recognized by the antibodies than those made by chloroplast targeting.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for generating a deglycosylated polypeptide of interest in a plant, comprising:
   (a) introducing into a plant cell a first nucleic acid comprising a first nucleotide sequence encoding a bacterial PNGase F polypeptide fusion protein comprising a plant signal peptide, wherein the first nucleotide sequence is operably linked to a promoter such that when the promoter is activated, the bacterial PNGase F polypeptide is transiently expressed by infiltration; and
   (b) introducing into the plant cell a second nucleic acid comprising a second nucleotide sequence encoding the polypeptide of interest, wherein the second nucleotide sequence is operably linked to a second promoter such that when the second promoter is activated, the polypeptide of interest is expressed, wherein the nucleotide sequence encoding the polypeptide of interest includes a sequence that is not naturally found in the plant cell, and wherein the polypeptide of interest contains a glycosylation site and the polypeptide of interest is transiently expressed by infiltration,
   wherein the PNGase F polypeptide and the polypeptide of interest include an endoplasmic reticulum retention sequence, and
   wherein by action of the PNGase F polypeptide cleaves all N-linked glycans of the polypeptide of interest in vivo.

2. The method of claim 1, comprising simultaneously introducing the first and second nucleic acids into the plant cell.

3. The method of claim 1, wherein the first and second nucleic acids are present in the same nucleic acid construct.

4. The method of claim 1, wherein the plant cell is a *Nicotiana benthamiana* cell.

5. The method of claim 1, wherein the first nucleotide sequence is SEQ ID NO: 1.

6. The method of claim 1, wherein the PNGase F polypeptide is SEQ ID NO:2.

7. The method of claim 1, wherein the first and second nucleic acids are introduced into the plant cell via an *Agrobacterium* construct.

8. The method of claim 1, wherein the polypeptide of interest is a pharmaceutical protein.

9. The method of claim 1, wherein the polypeptide of interest is an enzyme.

* * * * *

SEQUENCE LISTING

```
<160> NUMBER OF SEQ ID NOS: 12

<210> SEQ ID NO 1
<211> LENGTH: 1068
<212> TYPE: DNA
<213> ORGANISM: Artificial Sequence
<220> FEATURE:
<223> OTHER INFORMATION: recombinant DNA

<400> SEQUENCE: 1
atgggtttcg tgctgttctc tcagcttcca tctttccttt tggtgtctac ccttcttctg      60
ttccttgtga tttctcattc ttgcagagct gctccagctg ataacaccgt gaacattaag     120
accttcgata aggtgaagaa cgctttcggt gatggtcttt ctcaatctgc tgagggaact     180
tttaccttcc ctgctgatgt gactaccgtt aagaccatca agatgttcat caagaacgag     240
tgccctaaca agacttgtga tgagtgggat aggtacgcta atgtgtacgt gaagaacaag     300
actactggtg agtggtatga gatcggtaga ttcattactc cttactgggt gggaactgag     360
aagcttccta gaggtcttga gattgatgtg accgatttca agtctctgct gtctggtaat     420
accgagctta agatctacac cgagacttgt cttgctaagg gtagagagta ctccgttgat     480
ttcgatattg tgtacggaac ccctgattac aagtactcag ctgttgttcc tgtgatccag     540
tacaacaagt ctagcattga tggtgtgcca tacggtaagg ctcatactct tggtctgaag     600
aagaacattc agttgcctac taacaccgag aaggcttatc ttaggaccac tatttctggt     660
tggggtcatg ctaagcctta tgatgctggt tctagaggtt gtgctgagtg gtgttttagg     720
actcatacca ttgctatcaa caacgctaac actttccagc atcagcttgg tgctcttggt     780
tgttctgcta accctattaa caaccagtct cctggtaatt gggctcctga tagagctggt     840
tggtgtcctg gtatggctgt tcctactagg attgatgtgc tgaacaactc tcttaccggt     900
tctacattca gctacgagta caagttccag tcttggacta caacggtac taacggtgat      960 gctttctacg ctattagctc tttcgtgatc gctaagtcta atacccctat ttctgctcct    1020
gtggtgacca atgattacaa ggatgatgat gataaggatg agctttag                 1068

<210> SEQ ID NO 2
<211> LENGTH: 355
<212> TYPE: PRT
<213> ORGANISM: Artificial Sequence
<220> FEATURE:
<223> OTHER INFORMATION: recombinant protein

<400> SEQUENCE: 2
```

```
Met Gly Phe Val Leu Phe Ser Gln Leu Pro Ser Phe Leu Leu Val Ser
1               5                   10                  15

Thr Leu Leu Leu Phe Leu Val Ile Ser His Ser Cys Arg Ala Ala Pro
            20                  25                  30

Ala Asp Asn Thr Val Asn Ile Lys Thr Phe Asp Lys Val Lys Asn Ala
            35                  40                  45

Phe Gly Asp Gly Leu Ser Gln Ser Ala Glu Gly Thr Phe Thr Phe Pro
    50                  55                  60

Ala Asp Val Thr Thr Val Lys Thr Ile Lys Met Phe Ile Lys Asn Glu
65                  70                  75                  80

Cys Pro Asn Lys Thr Cys Asp Glu Trp Asp Arg Tyr Ala Asn Val Tyr
                85                  90                  95

Val Lys Asn Lys Thr Gly Glu Trp Tyr Glu Ile Gly Arg Phe Ile
                100                 105                 110

Thr Pro Tyr Trp Val Gly Thr Glu Lys Leu Pro Arg Gly Leu Glu Ile
            115                 120                 125

Asp Val Thr Asp Phe Lys Ser Leu Leu Ser Gly Asn Thr Glu Leu Lys
            130                 135                 140

Ile Tyr Thr Glu Thr Cys Leu Ala Lys Gly Arg Glu Tyr Ser Val Asp
145                 150                 155                 160

Phe Asp Ile Val Tyr Gly Thr Pro Asp Tyr Lys Tyr Ser Ala Val Val
                165                 170                 175

Pro Val Ile Gln Tyr Asn Lys Ser Ser Ile Asp Gly Val Pro Tyr Gly
                180                 185                 190

Lys Ala His Thr Leu Gly Leu Lys Lys Asn Ile Gln Leu Pro Thr Asn
            195                 200                 205

Thr Glu Lys Ala Tyr Leu Arg Thr Thr Ile Ser Gly Trp Gly His Ala
            210                 215                 220

Lys Pro Tyr Asp Ala Gly Ser Arg Gly Cys Ala Glu Trp Cys Phe Arg
225                 230                 235                 240

Thr His Thr Ile Ala Ile Asn Asn Ala Asn Thr Phe Gln His Gln Leu
                245                 250                 255

Gly Ala Leu Gly Cys Ser Ala Asn Pro Ile Asn Asn Gln Ser Pro Gly
            260                 265                 270

Asn Trp Ala Pro Asp Arg Ala Gly Trp Cys Pro Gly Met Ala Val Pro
            275                 280                 285

Thr Arg Ile Asp Val Leu Asn Asn Ser Leu Thr Gly Ser Thr Phe Ser
            290                 295                 300

Tyr Glu Tyr Lys Phe Gln Ser Trp Thr Asn Asn Gly Thr Asn Gly Asp
305                 310                 315                 320

Ala Phe Tyr Ala Ile Ser Ser Phe Val Ile Ala Lys Ser Asn Thr Pro
                325                 330                 335

Ile Ser Ala Pro Val Val Thr Asn Asp Tyr Lys Asp Asp Asp Lys
            340                 345                 350

Asp Glu Leu
        355

<210> SEQ ID NO 3
<211> LENGTH: 30
<212> TYPE: PRT
<213> ORGANISM: Nicotiana benthamiana

<400> SEQUENCE: 3

Met Gly Phe Val Leu Phe Ser Gln Leu Pro Ser Phe Leu Leu Val Ser
1               5                   10                  15
```

Thr Leu Leu Leu Phe Leu Val Ile Ser His Ser Cys Arg Ala
        20                  25                  30

<210> SEQ ID NO 4
<211> LENGTH: 8
<212> TYPE: PRT
<213> ORGANISM: Artificial Sequence
<220> FEATURE:
<223> OTHER INFORMATION: FLAG sequence

<400> SEQUENCE: 4

Asp Tyr Lys Asp Asp Asp Asp Lys
1               5

<210> SEQ ID NO 5
<211> LENGTH: 4
<212> TYPE: PRT
<213> ORGANISM: Artificial Sequence
<220> FEATURE:
<223> OTHER INFORMATION: synthetic sequence

<400> SEQUENCE: 5

Lys Asp Glu Leu
1

<210> SEQ ID NO 6
<211> LENGTH: 39
<212> TYPE: PRT
<213> ORGANISM: Cucumber Necrosis Virus

<400> SEQUENCE: 6

Met Leu Ile Ala His Pro Gln Ala Phe Pro Gly Ala Ile Ala Ala Pro
1 5 10 15

Ile Ser Tyr Ala Tyr Ala Val Lys Gly Arg Lys Pro Arg Phe Gln Thr
20 25 30

Ala Lys Gly Ser Val Arg Ile
35

<210> SEQ ID NO 7
<211> LENGTH: 79
<212> TYPE: DNA
<213> ORGANISM: Artificial Sequence
<220> FEATURE:
<223> OTHER INFORMATION: oligonucleotide sequence

<400> SEQUENCE: 7
agtcttaatt aaatgcttat tgctcaccca caagctttcc caggagctat tgctgctcca 60
atttcttacg cttacgctg 79

<210> SEQ ID NO 8
<211> LENGTH: 80
<212> TYPE: DNA
<213> ORGANISM: Artificial Sequence
<220> FEATURE:
<223> OTHER INFORMATION: oligonucleotide sequence

<400> SEQUENCE: 8
gagtccgtct caaatcctca cagatccctt agcagtctgg aaccttggct tcctaccctt 60
cacagcgtaa gcgtaagaaa 80

<210> SEQ ID NO 9
<211> LENGTH: 31
<212> TYPE: DNA

```
<213> ORGANISM: Artificial Sequence
<220> FEATURE:
<223> OTHER INFORMATION: Primer

<400> SEQUENCE: 9
agtcttaatt aaatgcttat tgctcaccca c                                31

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
gagtccgtct caaatcctca cagat                                       25

<210> SEQ ID NO 11
<211> LENGTH: 35
<212> TYPE: DNA
<213> ORGANISM: Artificial Sequence
<220> FEATURE:
<223> OTHER INFORMATION: Primer

<400> SEQUENCE: 11
gagtccgtct cagattaaca acgatttctg caagc                            35

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
gagtcctcga gtcagtggtg gtgatggtga tga                              33
```